(12) United States Patent
Lauerhaas et al.

(10) Patent No.: US 7,100,304 B2
(45) Date of Patent: Sep. 5, 2006

(54) MEGASONIC CLEANER AND DRYER

(75) Inventors: Jeffrey M. Lauerhaas, Leuven (BE); Thomas J. Nicolosi, Jr., Mission Viejo, CA (US); Paul Mertens, Bonheiden (BE); William Fyen, Heverlee (BE)

(73) Assignee: Akrion Technologies, Inc., Wilmington, DE (US)

( * ) Notice: Subject to any disclaimer, the term of this patent is extended or adjusted under 35 U.S.C. 154(b) by 13 days.

(21) Appl. No.: 10/864,927

(22) Filed: Jun. 10, 2004

(65) Prior Publication Data

US 2004/0221473 A1 Nov. 11, 2004

Related U.S. Application Data

(62) Division of application No. 10/171,426, filed on Jun. 12, 2002, now Pat. No. 6,754,980.

(60) Provisional application No. 60/297,736, filed on Jun. 12, 2001, provisional application No. 60/304,920, filed on Jul. 11, 2001, provisional application No. 60/315,725, filed on Aug. 30, 2001.

(51) Int. Cl.
*E21B 47/022* (2006.01)

(52) U.S. Cl. ............................. 34/312; 34/58; 134/95.2

(58) Field of Classification Search .................. 34/594, 34/107, 108, 667, 58, 312; 134/184, 56 R, 134/902, 95.2, 102.3, 153, 148

See application file for complete search history.

(56) References Cited

U.S. PATENT DOCUMENTS

| | | | | |
|---|---|---|---|---|
| 4,178,188 | A | * | 12/1979 | Dussault et al. |
| 4,326,553 | A | * | 4/1982 | Hall |
| 4,401,131 | A | * | 8/1983 | Lawson |
| 4,537,511 | A | * | 8/1985 | Frei |
| 4,902,350 | A | * | 2/1990 | Steck |
| 5,427,622 | A | * | 6/1995 | Stanasolovick et al. |
| 5,518,542 | A | * | 5/1996 | Matsukawa et al. |
| 5,656,097 | A | * | 8/1997 | Olesen et al. |
| 5,800,626 | A | * | 9/1998 | Cohen et al. |
| 5,849,104 | A | * | 12/1998 | Mohindre et al. |
| 5,964,954 | A | * | 10/1999 | Matsukawa et al. |

(Continued)

FOREIGN PATENT DOCUMENTS

DE 19833197 * 2/1999

(Continued)

OTHER PUBLICATIONS

IBM Technological Disclosure Bulletin vol. 37 No. 06A, Jun. 1994.

(Continued)

*Primary Examiner*—Henry Bennett
*Assistant Examiner*—Camtu Nguyen
(74) *Attorney, Agent, or Firm*—Brian L. Belles; Wolf, Block, Schorr & Solis-Cohen

(57) ABSTRACT

An apparatus for drying a generally flat substrate that has been cleaned has a rotatable support for supporting the substrate, a substrate drying assembly, and a controller. The substrate drying assembly includes a substrate drying assembly support arm, an outlet for applying liquid to an upper surface of the substrate, and an outlet for applying a drying vapor to the upper surface of the substrate. The substrate drying assembly is configured to position the liquid applying outlet and to position the vapor applying outlet above a portion of the substrate. The controller causes the substrate drying assembly to be retracted over the upper surface of the substrate at a faster rate near a center of the substrate than near a periphery of the substrate.

9 Claims, 26 Drawing Sheets

U.S. PATENT DOCUMENTS

| | | | | |
|---|---|---|---|---|
| 5,985,811 | A | * | 11/1999 | Masayuki et al. |
| 6,021,789 | A | * | 2/2000 | Akutsu et al. |
| 6,039,059 | A | * | 3/2000 | Bran |
| 6,140,744 | A | * | 10/2000 | Bran |
| 6,325,081 | B1 | * | 12/2001 | Miki et al. |
| 6,334,902 | B1 | * | 1/2002 | Mertens et al. |
| 6,468,362 | B1 | * | 10/2002 | Chen et al. .................. 134/26 |
| 2002/0029788 | A1 | * | 3/2002 | Verhaverbeke |

FOREIGN PATENT DOCUMENTS

| | | | |
|---|---|---|---|
| EP | 0 905746 | * | 3/1999 |
| EP | 905747 | * | 3/1999 |
| EP | 1 168419 | * | 1/2002 |
| JP | 61-179159 | * | 7/1986 |
| JP | 62-173935 | * | 7/1986 |
| WO | WO/98/02905 | * | 1/1998 |
| WO | WO/98/01896 | * | 3/1999 |
| WO | WO/99/16109 | * | 4/1999 |

OTHER PUBLICATIONS

"Ultra Pure Monitoring Guidelines 2000" Balaz Analytical Laboratory 1999.

"Study on Megasonic In Advanced Wet Cleaning Process", Electrochemical Society Proceedings vol. 95-20.

Nicolosi et al. "Front End of Wet Line Processing for Advanced Critical Cleans" Electrochemical Society Proceedings Honolulu 1999.

Yi Wu "Development of an Experimentally Validated Model of Megasonic Cleaning" Doctoral Thesis 1997.

Marc Heyns, et al. Ultra Clean Processing of Silicon Surfaces 2000 Scitec Publications, Ltd.

Paul W. Mertens, et al., "A high-performance drying method enabling clustered single wafer wet cleaning."

* cited by examiner

TRAJECTORY OF LIQUID

MEGASONIC CLEANER AND DRYER

CROSS REFERENCE TO RELATED APPLICATION

This application is a divisional application of Ser. No. 10/171,426 filed Jun. 12, 2002 now U.S. Pat. No. 6,754,980 which in turn claimed the benefit of U.S. Provisional Application No. 60/297,736, filed Jun. 12, 2001, and claimed the benefit of U.S. Provisional Application No. 60/304,920, filed Jul. 11, 2001, and claimed the benefit of U.S. Provisional Application No. 60/315,725, filed Aug. 30, 2001, the entirety of all of which are hereby incorporated by reference

BACKGROUND OF THE INVENTION

1. Field of the Invention

This invention relates to an apparatus and method for cleaning semiconductor substrates or other such items requiring extremely high levels of cleanliness.

2. Description of the Related Art

Semiconductor substrates can be cleaned by propagating acoustic energy, such as megasonic energy, into a layer of cleaning solution on the surface of the substrate. Megasonic cleaning systems use this cleaning solution layer to propagate megasonic energy, i.e. acoustic energy at frequencies much greater than ultrasonic. This energy is directed toward the surface of the substrate and thereby removes, safely and effectively, particles from the substrate surface without the negative side effects associated with ultrasonic cleaning.

In the past, such cleaning systems have been designed to process substrates in batches, typically cleaning 25 substrate at once. The benefit of this batch cleaning became less important as substrate size increased because single substrate capacity increased. Also, substrate processors began working with more delicate devices, which required more careful handling than was possible in batch cleaning. The greater value per substrate and the more delicate nature of the devices produced on the substrates created a great need for single wafer processing equipment.

Single substrate megasonic cleaning equipment for processing the larger substrates carrying more delicate devices have been developed to meet this need. One such single substrate cleaning system incorporates a probe and a transducer and is described in U.S. Pat. No. 6,140,744 and commercially available from Verteq Inc. of Santa Ana, Calif. One cleaning apparatus described therein comprises an elongate probe configured to propagate megasonic energy to a surface of a substrate by way of a meniscus of liquid extending between the probe and the substrate. Because the energy is transmitted through a meniscus of liquid, the process is a "set" process and it requires the probe to be positioned very close to the substrate surface.

After this "wet" cleaning process, the substrate must be dried prior to further processing. Various methods of drying the substrate have been tried and have generally involved spinning the substrate and thereby forcing the liquid off the substrate surface via centrifugal forces arising from the spinning. Unfortunately, this drying method has its drawbacks, such as the tendency of liquid on a surface to leave behind residue, e.g. water spots. In the past, such spots were not of great concern to the simpler devices being produced on the substrates. However, as already mentioned, the devices processed on substrates have become more delicate, and therefore more sensitive to contaminants of all kinds, including water spots. Moreover, substrate processors have become more aware of sources of process variation, which translate into variation in performance of the devices and yield variation. One such source of these variations is contaminants, including drying residue. Therefore, careful control of the drying conditions has been investigated by some.

European patent application publication EP0905747A1 to IMEC discloses a drying apparatus that exploits rotational and Marangoni effects to improve drying performance. As mentioned above, the rotation of the substrate subjects the liquid to centrifugal forces, which tend to force the liquid from the center of the substrate toward its edge, and ultimately off of the surface. Simultaneously, a surface tension reducing vapor creates the so called Marangoni effect that reduces the tendency of the liquid to adhere to the substrate surface, i.e. reduces the liquid surface tension. This reduces the tendency of the liquid to remain on the substrate surface long enough to evaporate from the surface and therefore helps to produce a residue free drying process. While the IMEC apparatus has achieved satisfactory substrate drying results in the laboratory, the concept has not been implemented into a commercial application.

Another issue presented by wet spin cleaning and drying of substrates is the containment and disposal of the process liquids involved, for example, various acids, bases, solvents, and de-ionized water. Some of these liquids may harm workers or damage other equipment in the vicinity of the cleaning apparatus if the workers or equipment come into contact with the process liquids. Thus, full containment and removal of the process liquids is necessary to maintain a safe working environment and protect valuable equipment.

However, a critical design consideration for any machine in substrate processing is process time, or through-put. This is in part because substrate processing must be done in very clean, and thus very expensive, fabrication facilities. As a result, substrate processors prefer to maximize the output of existing facilities rather than expanding those facilities or building new ones. Thus, fast through-put is preferred.

Therefore, a need exists for an improved cleaning method and apparatus that will improve the drying performance in a single wafer processing application and will improve throughput for performing substrate cleaning and drying operations.

SUMMARY OF THE INVENTION

In one embodiment, the present invention is a method of cleaning and drying a generally flat substrate positioned on a rotatable support is provided. A transmitter is positioned closely spaced above an upper surface of the substrate. Fluid is applied to the substrate to create a meniscus between the transmitter and the rotating substrate. Megasonic energy is applied to the transmitter to cause it to propagate megasonic energy through the meniscus to the substrate to loosen particles on the substrate while the substrate is rotating at a first rate. The transmitter is retracted. A substrate drying assembly support arm of a substrate drying assembly is moved into position closely spaced above the substrate. The substrate drying assembly includes an outlet for applying liquid to the upper surface of the substrate and includes an outlet for applying a drying vapor to the upper surface of the substrate. The substrate drying assembly support arm is moved into place as the transmitter is being retracted.

In another embodiment, a method of cleaning and drying a generally flat substrate positioned on a rotatable support is provided. A surface of the substrate is cleaned. A substrate drying assembly support arm of a substrate drying assembly is moved into position closely spaced above the substrate.

The substrate drying assembly includes an outlet for applying liquid to the upper surface of the substrate and includes an outlet for applying a drying vapor to the upper surface of the substrate. The substrate drying assembly support arm is retracted radially outwardly at a retraction rate to a periphery of the substrate while liquid is applied to the substrate through the liquid outlet. Then, the drying vapor is applied to the substrate to dry the substrate. The substrate drying assembly support arm is retracted at a substrate-center retraction rate near the center of the substrate and a substrate-periphery retraction rate near the periphery of the substrate. The substrate-center retraction rate is faster than the substrate-periphery retraction rate.

In another embodiment, a method of cleaning and drying a generally flat substrate positioned on a rotatable support is provided. A surface of the substrate is cleaned. A substrate drying assembly support arm of a substrate drying assembly is moved into position closely spaced above the substrate. The substrate drying assembly includes an outlet for applying liquid to the upper surface of the substrate and includes an outlet for applying a drying vapor to the upper surface of the substrate. The substrate drying assembly support arm is retracted radially outwardly at a retraction rate to a periphery of the substrate while liquid is applied to the substrate through the liquid outlet. Then, the drying vapor is applied to the substrate to dry the substrate. At a location between the center of the substrate and the periphery of the substrate, the retraction rate of the substrate drying assembly support arm is greater than the retraction rate near the center of the substrate and greater than the retraction rate near the periphery of the substrate.

In another embodiment, a method of cleaning and drying a generally flat substrate positioned on a rotatable support is provided. A surface of the substrate is cleaned. A substrate drying assembly support arm of a substrate drying assembly is moved into position closely spaced above the substrate. The substrate drying assembly includes an outlet for applying liquid to the upper surface of the substrate and includes an outlet for applying a drying vapor to the upper surface of the substrate. The substrate drying assembly support arm is retracted radially outwardly at a retraction rate to a periphery of the substrate while liquid is applied to the substrate through the liquid outlet. Then, the drying vapor is applied to the substrate to dry the substrate. The substrate is rotated in a range between about 50 rpm and about 1,000 rpm while the retraction rate is in the range between about 1 mm per second and about 20 mm per second.

In another embodiment, a method of drying a generally flat substrate that has been cleaned is provided, where the substrate has been positioned on a rotatable support. At least one of a blanket substrate drying process window if the substrate has a blanket portion or a patterned substrate drying process window if the substrate has a patterned portion is selected. A substrate drying assembly support arm of a substrate drying assembly is moved into position closely spaced above the substrate. The substrate drying assembly includes an outlet for applying liquid to an upper surface of the substrate and includes an outlet for applying a drying vapor to the upper surface of the substrate. The substrate is rotated. The substrate drying assembly support arm is retracted radially outwardly according to the selected drying process window to a periphery of the substrate while liquid is applied to the substrate through the liquid applying outlet. Then, the drying vapor being applied to the substrate to dry the substrate.

In another embodiment, a method of drying a generally flat substrate that has been cleaned is provided, where the substrate is positioned on a rotatable support. A substrate drying assembly support arm of a substrate drying assembly is moved into position closely spaced above the substrate. The substrate drying assembly includes an outlet for applying liquid to an upper surface of the substrate and includes an outlet for applying a drying vapor to the upper surface of the substrate. The substrate drying assembly support arm is retracted radially outwardly at a retraction rate to a periphery of the substrate while liquid is being applied to the substrate through the liquid applying outlet. Then, the drying vapor is applied to the substrate to dry the substrate. The substrate drying assembly support arm is retracted at a substrate-center retraction rate near the center of the substrate and a substrate-periphery retraction rate near the periphery of the substrate. The substrate-center retraction rate is faster than the substrate-periphery retraction rate.

In another embodiment, an apparatus for cleaning and drying a generally flat substrate includes a substrate support positioned within a process bowl, a transmitter, a fluid dispenser, a substrate drying assembly, and a controller. The transmitter is configured to be spaced above the substrate, to propagate megasonic energy, and to be extendable into and out of the process bowl. The fluid dispenser applies fluid to a surface of the substrate. The substrate drying assembly is configured to be spaced above the substrate. The substrate drying assembly includes an outlet for applying liquid to an upper surface of the substrate and an outlet for applying a drying vapor to the upper surface of the substrate. The substrate drying assembly is extendable into and out of the process bowl. The controller causes the transmitter and the substrate drying assembly to be extended from the edge of the process bowl to a position over the surface of the substrate, and causes the transmitter to be retracted from the process bowl as the substrate drying assembly is being extended.

In another embodiment, an apparatus for cleaning and drying a generally flat substrate comprises a rotatable support for supporting the substrate, a transmitter, a fluid dispenser, a substrate drying assembly, and a controller. The rotatable support is positioned within a process bowl. The transmitter is configured to be spaced above the substrate, to propagate megasonic energy, and to be extendable into and out of the process bowl. The fluid dispenser applies fluid to a surface of the substrate. The substrate drying assembly is configured to be spaced above the substrate. The substrate drying assembly includes an outlet for applying liquid to an upper surface of the substrate and an outlet for applying a drying vapor to the upper surface of the substrate. The substrate drying assembly is configured to be extendable into and out of the process bowl. The controller causes the transmitter and the substrate drying assembly to be extended from the edge of the process bowl to a position over the surface of the substrate. The controller also causes the transmitter and the substrate drying assembly to be retracted from a position over the surface of the substrate to the edge of the process bowl. The controller also causes the substrate to be rotated in a range of rates between about 50 revolutions per minute and about 1,000 revolutions per minute during the drying of the upper surface of the substrate. The controller also causes the substrate drying assembly to be retracted in a range of rates between about 1 mm per second and about 20 mm per second.

In another embodiment, an apparatus for drying a generally flat substrate that has been cleaned includes a rotatable support for supporting the substrate, a substrate drying assembly, and a controller. The substrate drying assembly includes an outlet for applying liquid to an upper surface of the substrate and an outlet for applying a drying vapor to the upper surface of the substrate. The substrate drying assembly is configured to position the liquid applying outlet and to position the vapor applying outlet above a portion of the substrate. The controller causes the substrate drying assembly to be retracted over the surface of the substrate at a range of rates up to and including a maximum rate. The maximum rate is increased as the rate at which the substrate is rotated is increased by about 0.5 mm per second for about each 100 increase in the revolutions per minute of the rotation of the substrate. The controller also is configured to cause the rotatable support to change the rate of rotation of the substrate while the substrate drying assembly is over the substrate.

In another embodiment, an apparatus for drying a generally flat substrate that has been cleaned includes a rotatable support for supporting the substrate, a substrate drying assembly, and a controller. The substrate drying assembly includes an outlet for applying liquid to an upper surface of the substrate and an outlet for applying a drying vapor to the upper surface of the substrate. The substrate drying assembly is configured to position the liquid applying outlet and to position the vapor applying outlet above a portion of the substrate. The controller applies at least one of a patterned substrate process window or a blanket substrate process window, causes the substrate drying assembly to be retracted over the surface of the substrate, and causes the rotatable support to change the rate of rotation of the substrate while the substrate drying assembly is over the substrate.

In another embodiment, an apparatus for drying a generally flat substrate that has been cleaned includes a rotatable support for supporting the substrate, a substrate drying assembly, and a controller. The substrate drying assembly includes a substrate drying assembly support arm, an outlet for applying liquid to an upper surface of the substrate, and an outlet for applying a drying vapor to the upper surface of the substrate. The substrate drying assembly is configured to position the liquid applying outlet and to position the vapor applying outlet above a portion of the substrate. The controller causes the substrate to be rotated in a range of rates between about 50 revolutions per minute and about 1,000 revolutions per minute during the drying of the upper surface of the substrate. The controller causes the substrate drying assembly support arm in a range of retraction rates between about 1 mm per second and about 20 mm per second.

In another embodiment, an apparatus for drying a generally flat substrate that has been cleaned has a rotatable support for supporting the substrate, a substrate drying assembly, and a controller. The substrate drying assembly includes a substrate drying assembly support arm, an outlet for applying liquid to an upper surface of the substrate, and an outlet for applying a drying vapor to the upper surface of the substrate. The substrate drying assembly is configured to position the liquid applying outlet and to position the vapor applying outlet above a portion of the substrate. The controller causes the substrate drying assembly to be retracted over the upper surface of the substrate at a faster rate near a center of the substrate than near a periphery of the substrate.

In another embodiment, an apparatus for drying a generally flat substrate that has been cleaned includes a rotatable support for supporting the substrate, a substrate drying assembly, and a splashguard. The rotatable support is rotatable at a first rate and a second rate, the second rate being much greater than the first rate. The substrate drying assembly includes an outlet for applying liquid to an upper surface of the substrate and an outlet for applying a drying vapor to the upper surface of the substrate. The splashguard prevents splash-back onto the substrate when the rotatable support is rotating at the second rate.

DETAILED DESCRIPTION OF THE PREFERRED EMBODIMENT

Figure 1:
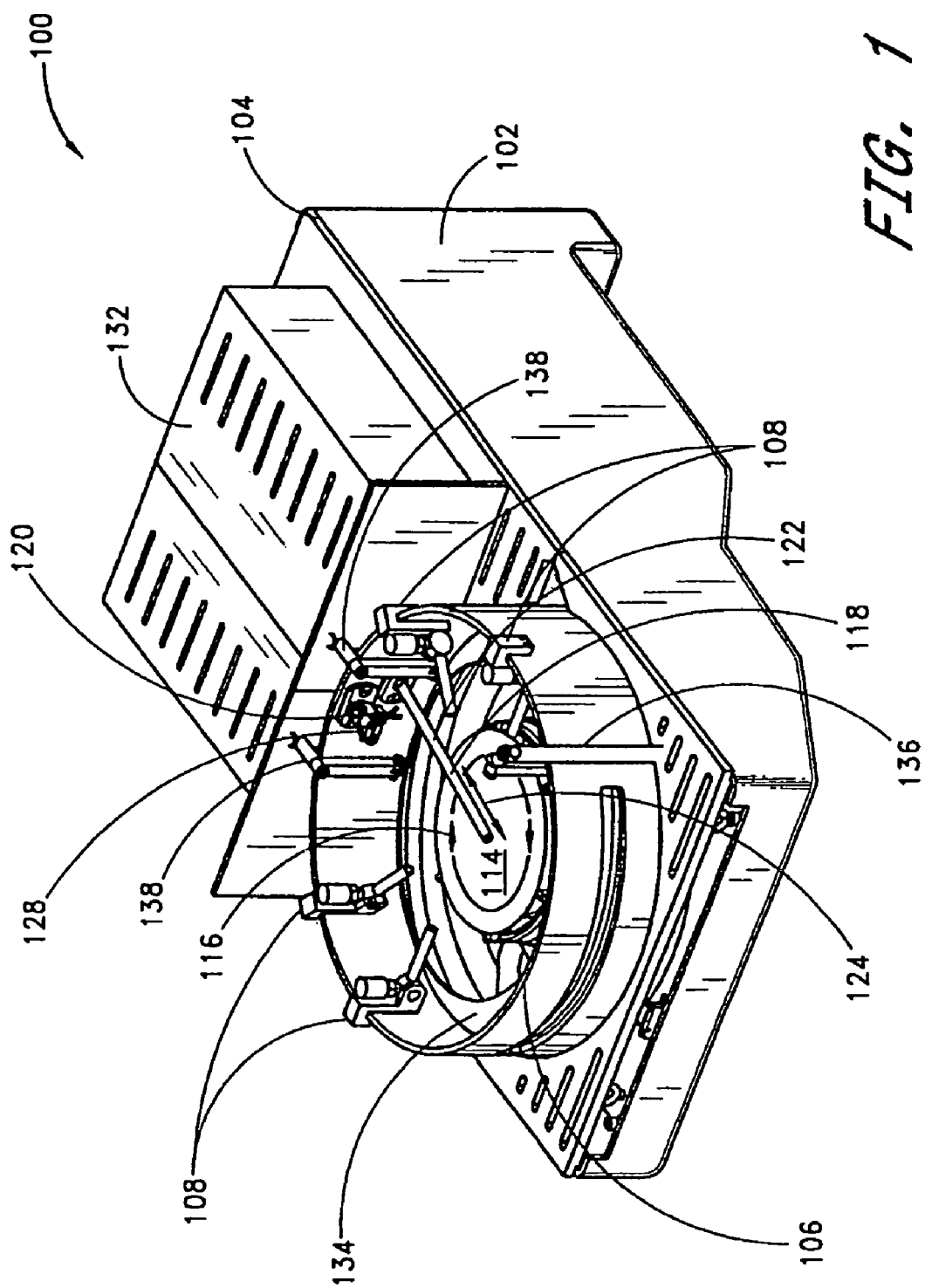
FIG. 1 is a schematic isometric view of one embodiment of the substrate cleaning apparatus.

FIGS. 1–6 illustrate one embodiment of a megasonic energy cleaning and drying apparatus 100 made in accordance with the present invention with a containment plenum 102 below and supporting an assembly main reference plate (shown in FIGS. 6–8, 9–11C), which is nested underneath a removable decktop 104. A process bowl 106 is nested within the containment plenum 102 and extends through a cut-out in the decktop 104. The bowl 106, which is preferably cylindrical or any other suitable shape, has a vertical portion that extends through the decktop cut-out to a desired height. The decktop cut-out is preferably the same shape as the bowl 106.

A plurality of dispensers 108 are mounted to the vertical portion of the bowl 106, i.e. the bowl side wall, and extend toward the bowl's center. Each of the dispensers 108 has an outlet through which fluid is dispensed. These dispensers 108 may be pivotably mounted to brackets which have the shape of an inverted "J", the inside curve of which is configured to receive the top surface of the bowl. In this way, the elevation of the dispenser may be fixed. The dispensers 108 are connected to gas or liquid supply lines (not shown) which provide cleaning media to the surface desired to be cleaned. The position of the dispensers with respect to the other components is relates to controlling the cleaning operation in some embodiments, and will be discussed in more detail below.

Figure 6:
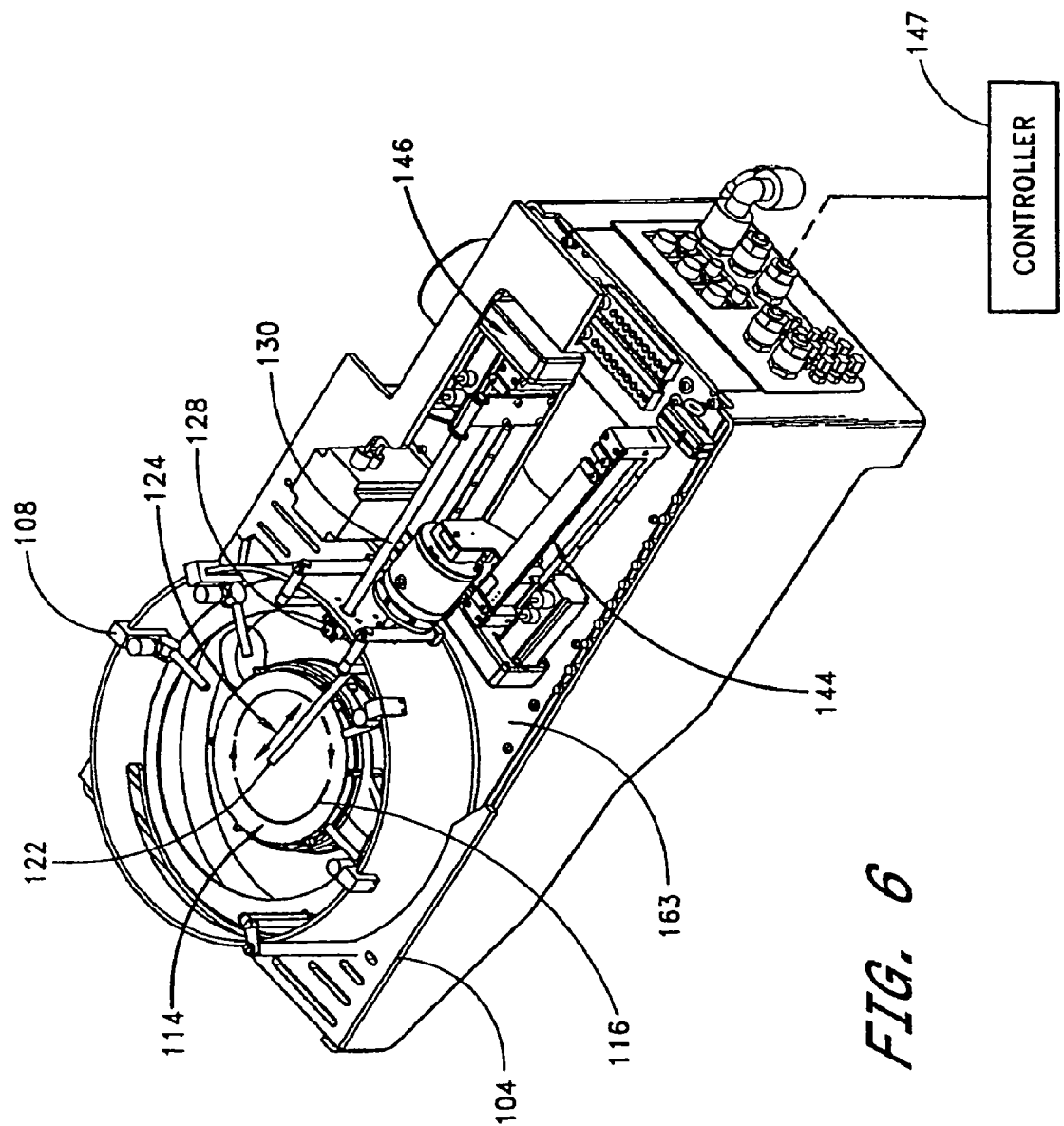
FIG. 6 is a isometric view of one embodiment of the substrate cleaning apparatus with the component cover removed and a portion of the removable decktop cut away.
Figure 7:
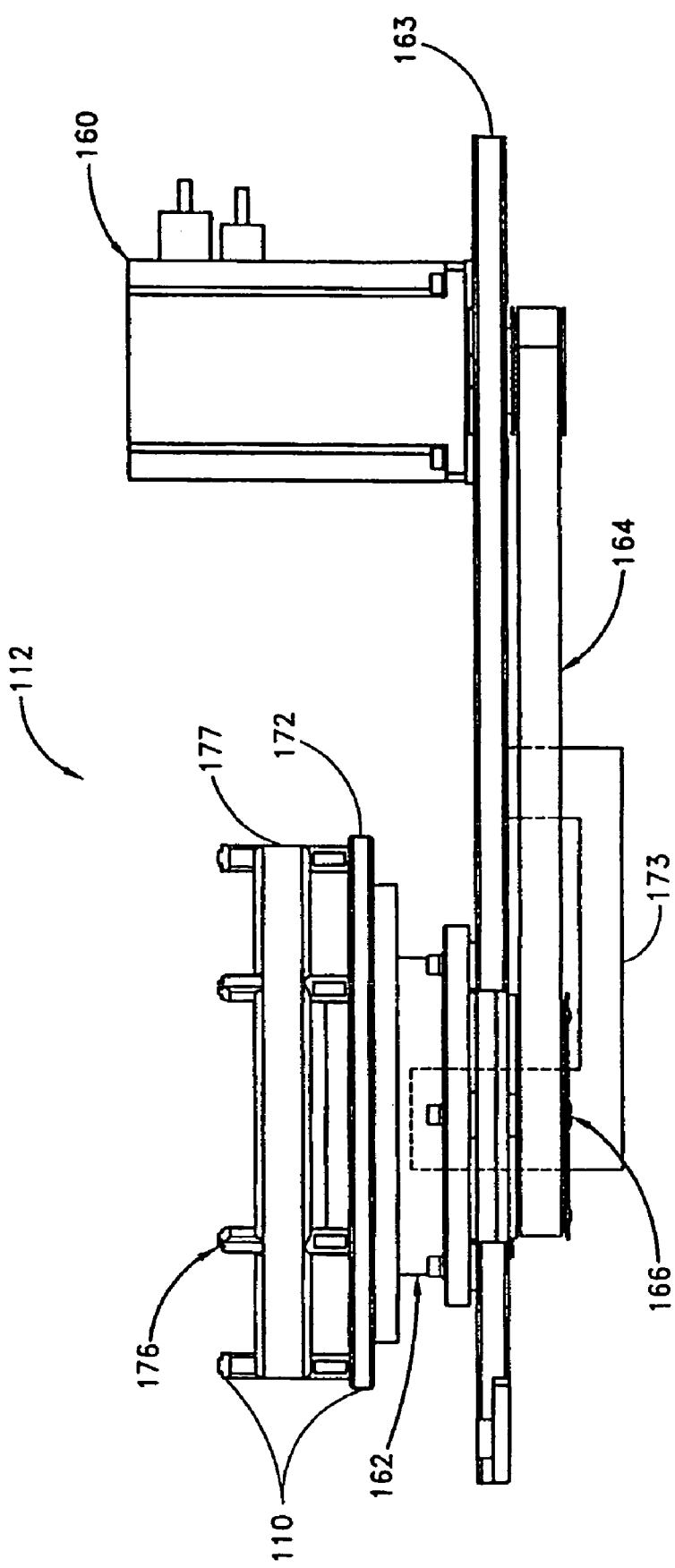
FIG. 7 is side elevation view of one embodiment of the substrate chuck and servomotor assembly.
Figure 8:
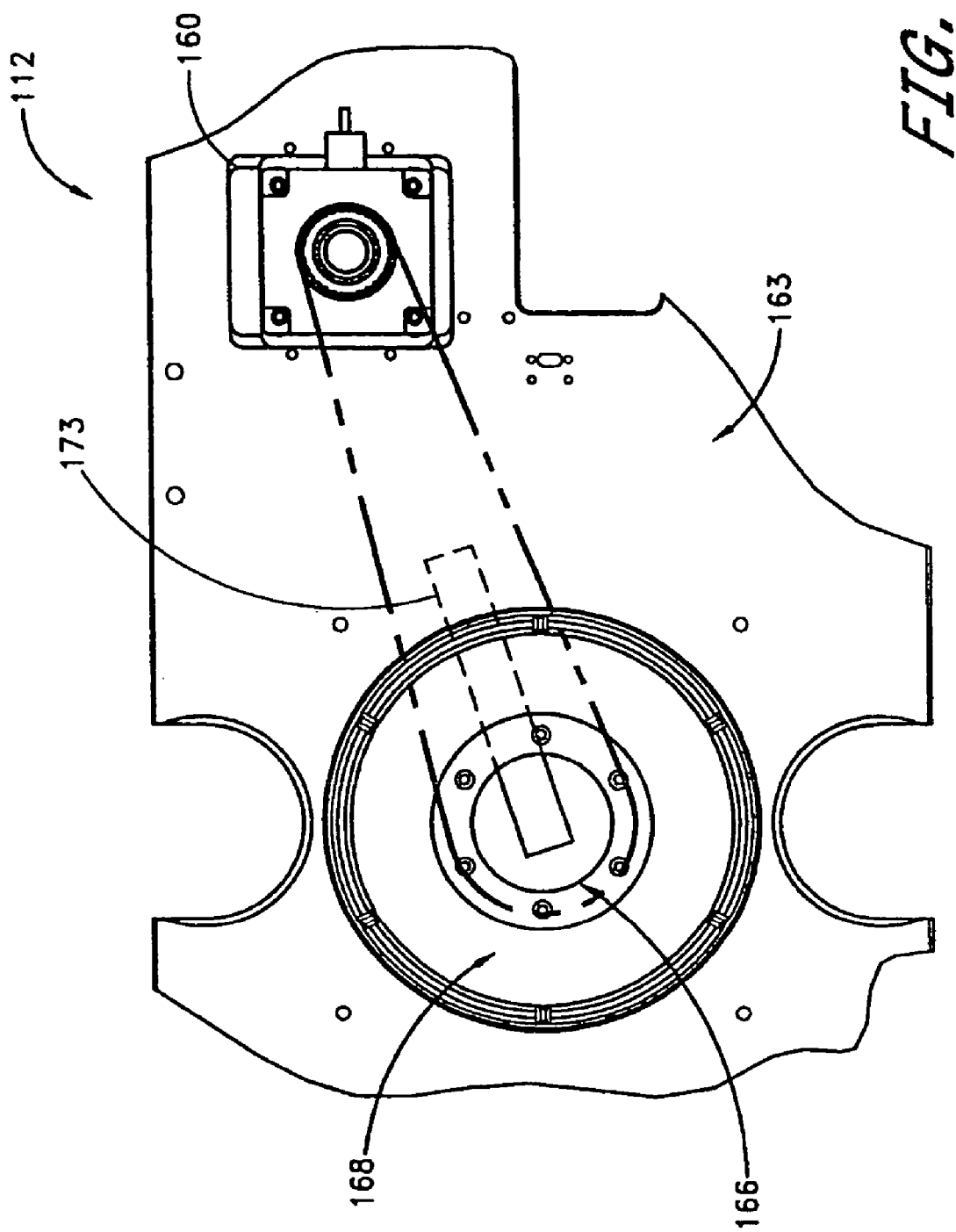
FIG. 8 is a top view of one embodiment of the substrate chuck and servo motor assembly of FIG. 7.
Figure 9A:
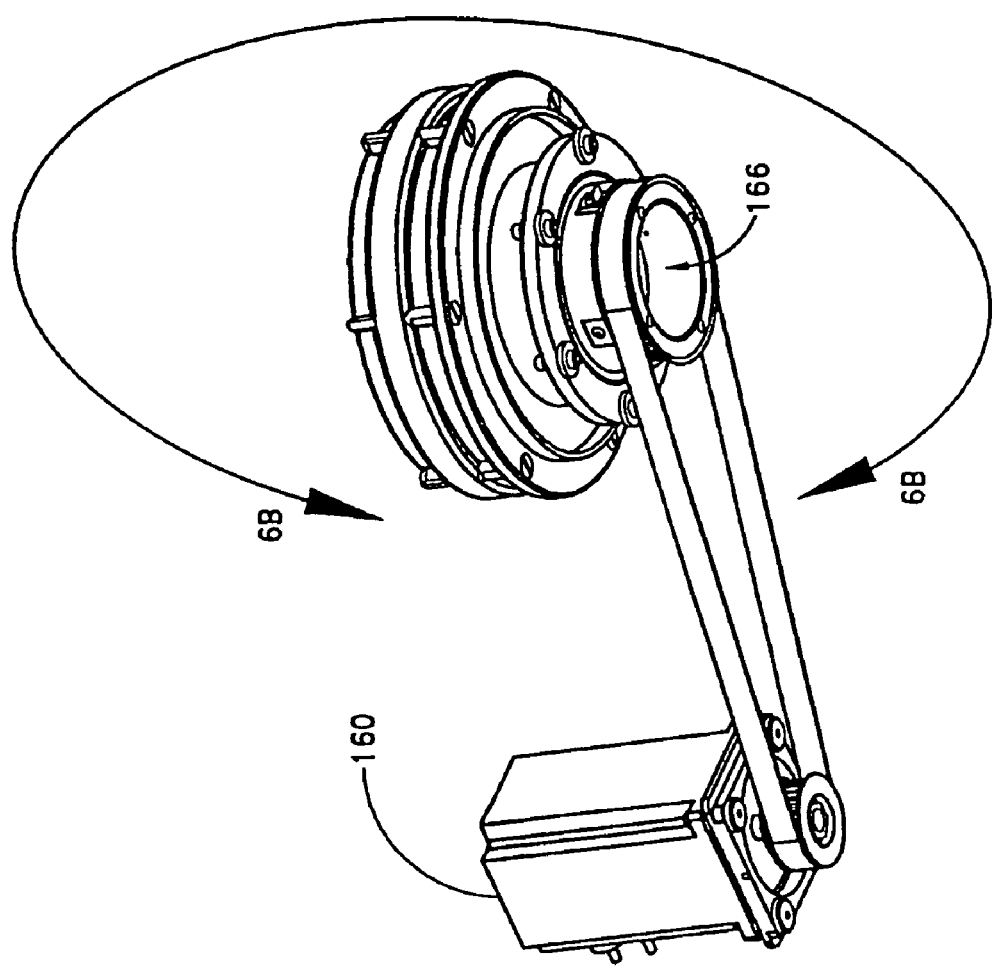
FIG. 9A is an isometric view of one embodiment of the substrate chuck assembly of the substrate cleaning system.
Figure 9B:
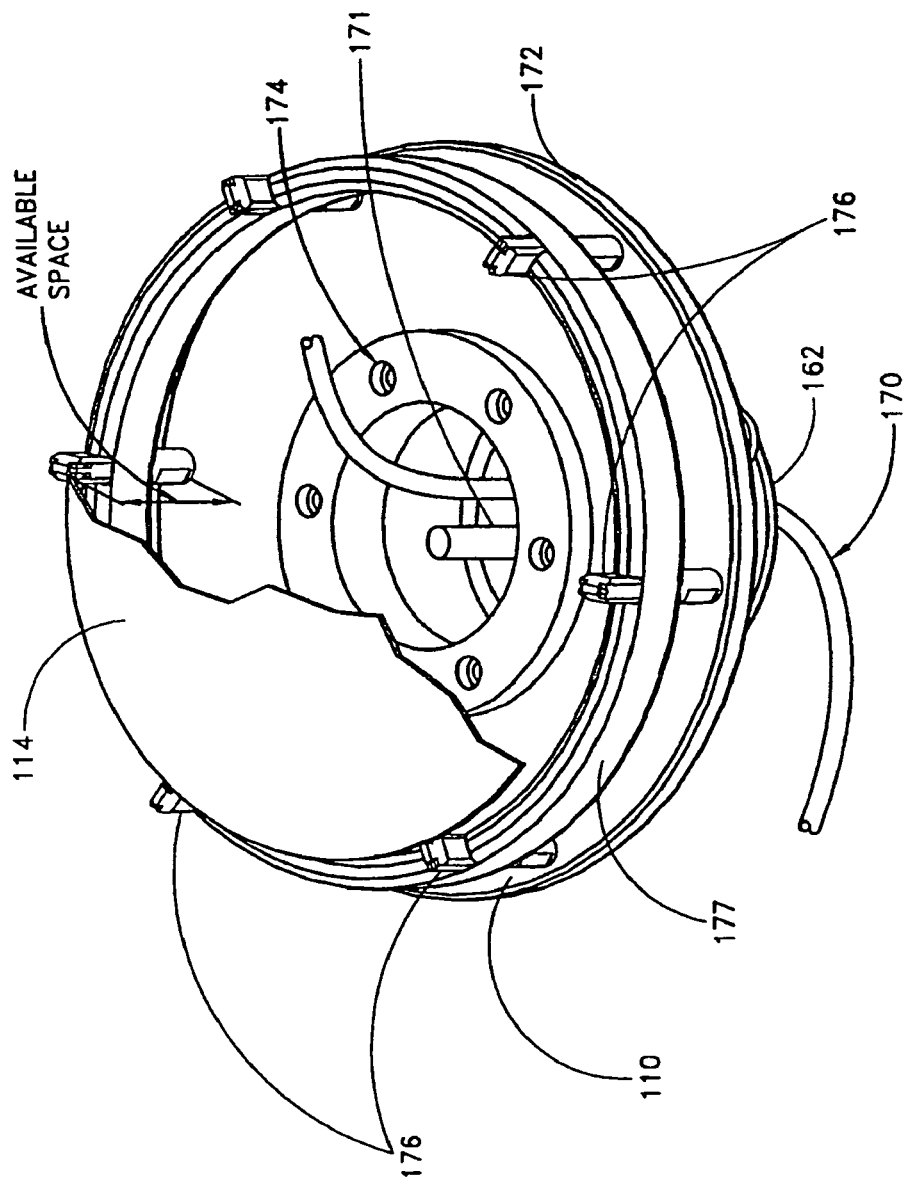
FIG. 9B is an isometric view of one embodiment of an open center chuck of the substrate chuck assembly shown in FIG. 9A.
Figure 12:
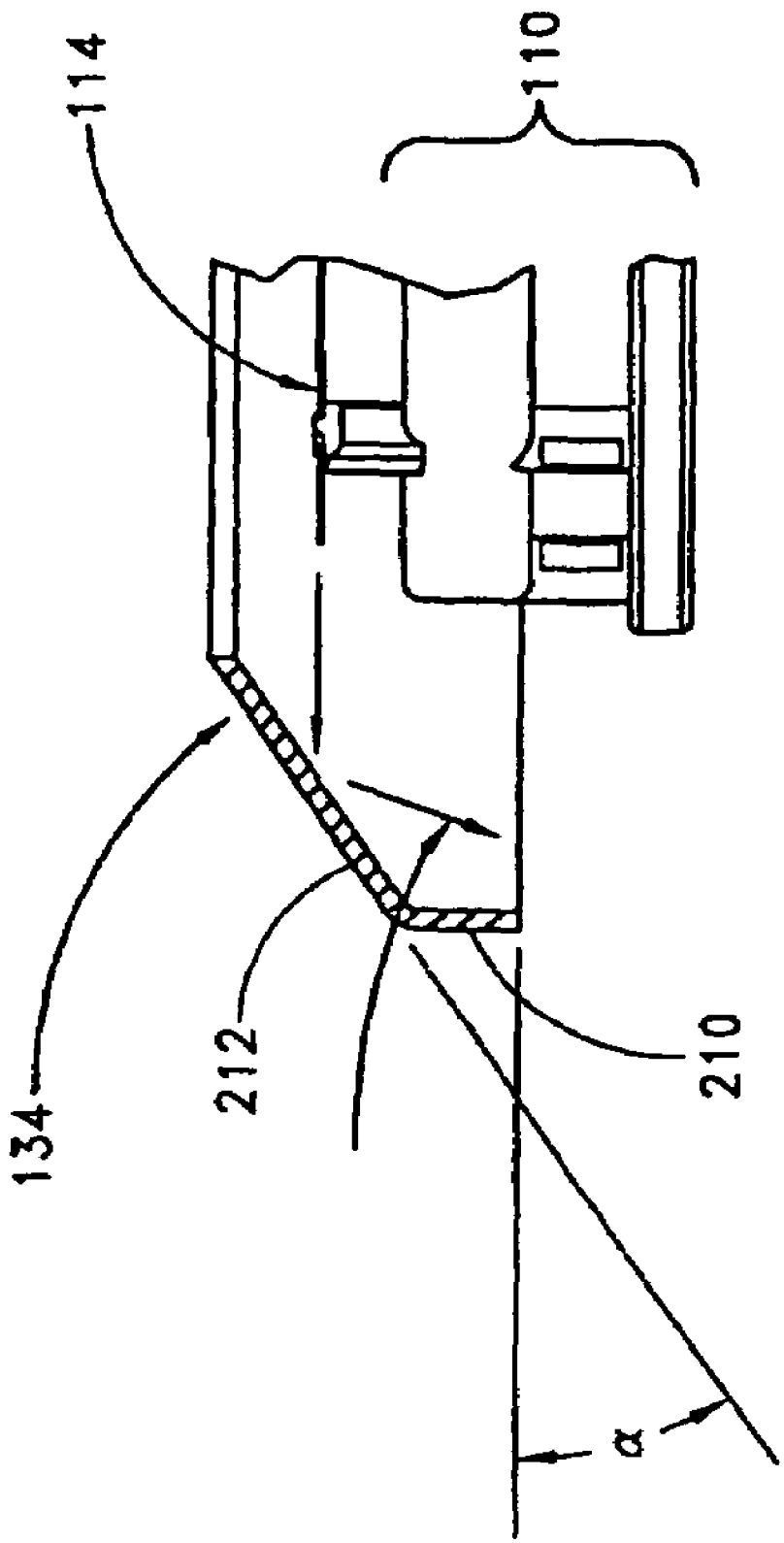
FIG. 12 is a partial view of one embodiment of the substrate chuck and moveable splash guard with the splash guard shown in cross-section.

A substrate chuck 110 of a substrate chuck assembly 112 is also positioned within the process bowl 106 and is configured to receive and support a substrate 114 during processing in the cleaning apparatus 100 (See FIGS. 7, 9B and 12). The chuck 110 and the dispensers 108 are positioned relative to one another so that when the substrate 114 is positioned on the chuck 110 the cleaning media dispensed by the dispensers 108 may be directed onto a surface of the substrate 114. The chuck 110 is rotatable with respect to the process bowl, as discussed in more detail below in connection with FIGS. 7 and 8. As shown in FIGS. 1 and 6, the substrate is rotated on the chuck 110 as indicated by arrows 116 during processing in the apparatus 100. The direction of the arrows 116 is not intended to indicate that the substrate 114 may be rotated in only one direction. The substrate may be rotated in the direction opposite to that shown in FIGS. 1 and 6 in accordance with the wafer cleaning and drying assembly 100.

The side wall of the bowl 106 near the rear-most portion of the bowl comprises at least one aperture. These apertures provide access to the processing chamber of the process bowl 106 for any of a number of processing devices, e.g., the aperture provides access for a cleaning assembly 118 and/or a substrate drying assembly 120, also referred to herein as the drying assembly 120. There may also be two or more apertures in the rear portion sidewall, one to provide access for the drying assembly 120 and one to provide access for the cleaning assembly 118. Other suitable processing devices can also be incorporated into the apparatus 100.

The cleaning assembly 118 may include a rod-like probe coupled to a megasonic transducer. As mentioned above, a rod-like probe coupled to a megasonic transducer is described in more detail in U.S. Pat. No. 6,140,744, which is hereby incorporated by reference. As described therein, a probe 122 is configured to propagate megasonic energy to the surface of the substrate 114 by way of a meniscus of liquid extending between the probe and the substrate 114 to loosen particles on the substrate. The probe 122 must be positioned close enough to the substrate 114 so that a meniscus of liquid extends between the probe and the substrate. Preferably this distance is about one-tenth of an inch, or about 2.5 millimeters, creating a meniscus of the same height except that the liquid also covers a small lower edge of the probe. In one form of the invention, the liquid forming the meniscus is applied to the surface of the substrate 114 by suitable dispensers 108. Although a rod-like probe is illustrated in connection with the preferred embodiment described herein, a transmitter of any suitable shape will also work.

Control of the liquid interface between the probe 122 and the substrate 114 (the meniscus) can enhance the cleaning performance of the cleaning and drying apparatus 100. There are several variables which influence the amount of energy that may be propagated through the liquid to the surface of the substrate 114, including the height of the meniscus, the absence or presence of surface waves impacting the probe 122, the fluid flow properties of the cleaning media, the ability to dispense the cleaning media in a pulsing (i.e., a flow-rate variable) fashion, the frequency of the acoustic energy applied to the probe, the availability of a dispenser to apply a loading media to the probe 122 to dampen the energy of the probe, and other factors.

The acoustic energy propagated through the meniscus can be controlled by carefully positioning the cleaning liquid dispensers so that the liquid that they dispense does not substantially interfere with the operation of the probe. Such interference can occur, for example, when the thickness of the meniscus proximate the probe varies substantially. This can occur, for example, if surface waves are created in the liquid meniscus proximate the probe 122. One way to reduce the interference of the dispensed liquid with the propagation of energy is to position the dispensers so that the dispenser nozzles dispense the cleaning liquid onto a portion of the substrate that is not near the probe. The dispensers 108 may be positioned at any desired location around the circumference of the bowl 106, and their location may be defined as a number of degrees between 0 and 360 with respect to a reference location, such as the probe 122 forming a part of the cleaning assembly 118. More specifically, if the probe 122 is the reference location, then 90 degrees is the location that is one-quarter the way around the bowl 106 from the probe in the clockwise direction as viewed from the top.

Propagation of energy through the meniscus can be controlled by creating a liquid dispenser location map for the substrate cleaning apparatus 100. A dispenser location map can be created by dividing the 360 degree range of cleaning dispenser locations around the circumference of the bowl 106 into at least two circumferential zones. The circumferential zones may or may not be physically distinct features of the process bowl 106. In one preferred embodiment, the range of nozzle positions is divided into five circumferential zones (see FIG. 2). A zone 150 can include the position of the probe 122, i.e., the reference location at zero degrees. The zone 150 could extend clockwise around the bowl 106 from about 315 degrees to about 90 degrees. A zone 152 can be located adjacent to the zone 150, extending clockwise around the bowl 106 from about 270 degrees to about 315 degrees. A zone 154 can be located adjacent to the zone 152, extending clockwise around the bowl 106 from about 235 degrees to about 270 degrees. A zone 156 can be located adjacent to the zone 154, extending clockwise around the bowl 106 from about 135 degrees to about 235 degrees. A zone 158 is located between the zone 156 and the zone 150, extending from about 90 degrees to about 135 degrees. In one embodiment, the cleaning fluid dispensers 108 are positioned in any of the zones 152, 154, 156, or 158. More preferably, the cleaning fluid dispensers 108 are positioned in any of zones 154, 156, or 158. Still more preferably, the cleaning fluid dispensers are positioned in either zone 154 or zone 158.

In another variation, the zone 150 can be subdivided into two sub-zones. The first sub-zone extends clockwise from about 315 degrees to about 45 degrees, and the second sub-zone extends from about 45 degrees to about 90 degrees. In this embodiment, the cleaning fluid dispensers 108 are positioned in any of the zones 152, 154, 156, 158, or the second sub-zone of the zone 150 extending from about 45 degrees to about 90 degrees. More preferably, the cleaning fluid dispensers 108 are positioned in any of zones 154, 156, or 158. Still more preferably, the cleaning fluid dispensers are positioned in either zone 154 or zone 158.

The cleaning fluid dispensers 108 dispense liquid in a direction that is preferably generally perpendicular to a vertical plane passing through the longitudinal axis of the probe 122. However, the dispensers may be made adjustable to a range of dispense angles with respect to the probe. For example, the dispensers 108 can be rotated about a vertical axis passing through the base of the dispenser 108. The range of rotation can be about thirty degrees to the right of and about thirty degrees to the left of a horizontal line perpendicular to the vertical plane passing through the probe 122. This may improve the control of the meniscus in one or more of the radial zones 152–158. For example, in the zone 152, an angle of thirty degrees to the right of the horizontal line perpendicular to the vertical plane passing through the probe 122 may be preferred.

Figure 2:
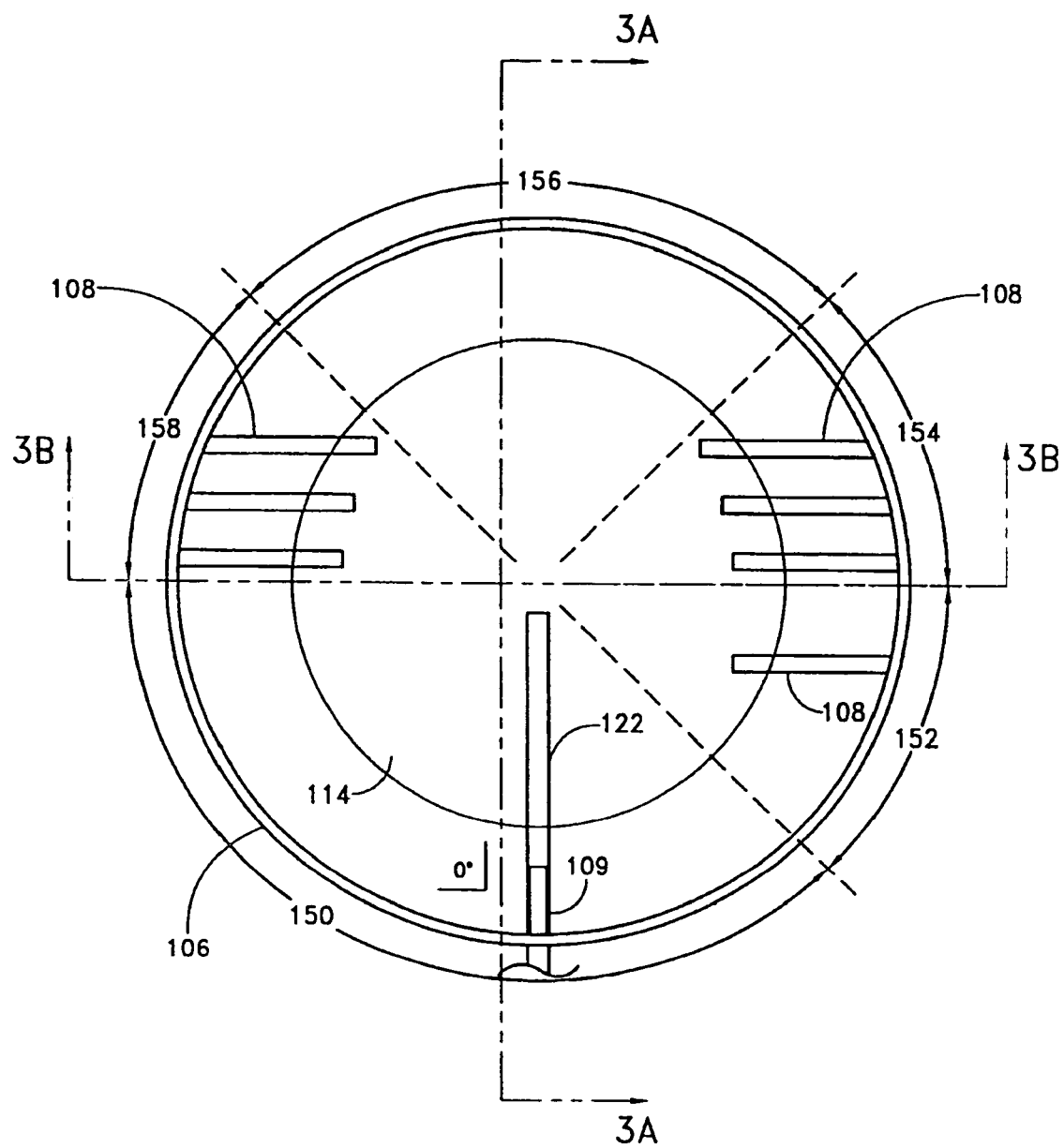
FIG. 2 is a schematic top view of one embodiment of a processing chamber showing a liquid dispenser location map for the substrate cleaning apparatus of FIG. 1.
Figure 3A:
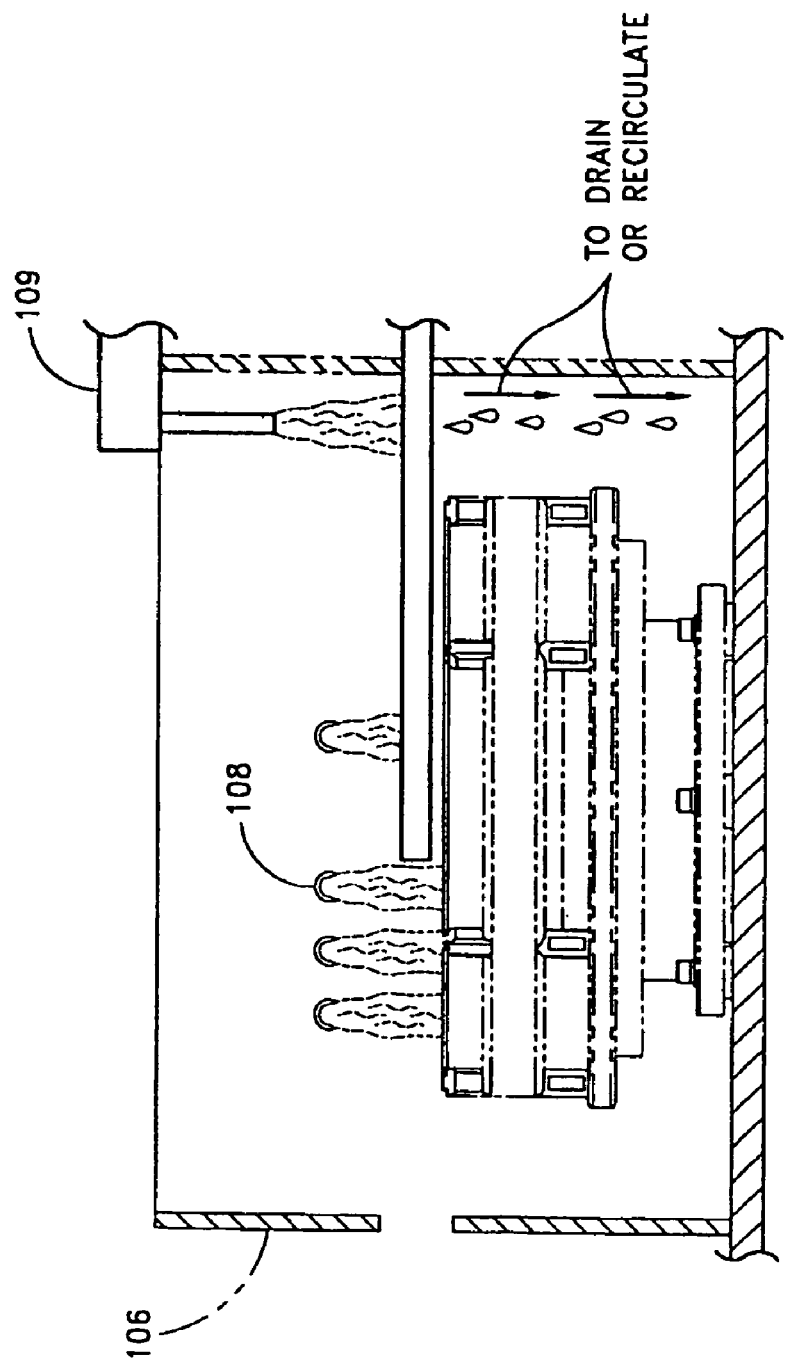
FIG. 3A is a cross-sectional view of one embodiment of the processing chamber of FIG. 2 taken along section lines 3A—3A.
Figure 3B:
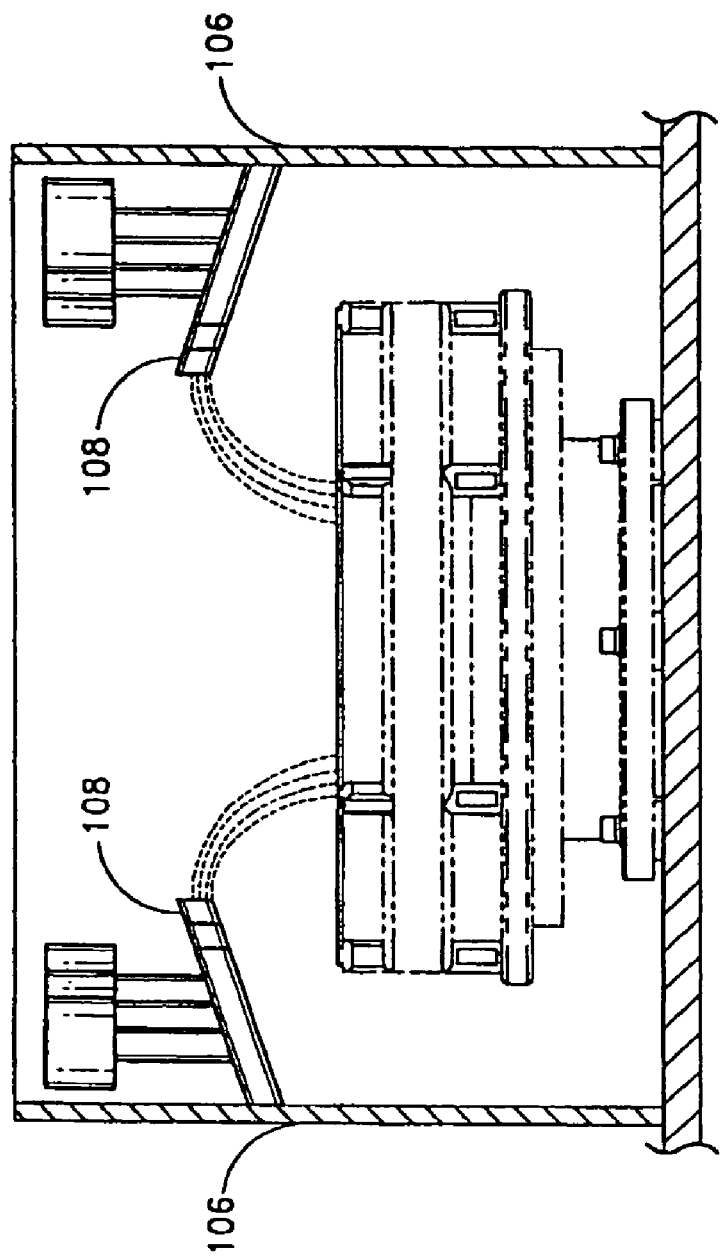
FIG. 3B is a cross-section view of one embodiment of the processing chamber of FIG. 2 taken along section lines 3B—3B.

As shown in FIGS. 2 and 3A, a transmitter-loading dispenser 109 can be configured to dispense liquid directly onto the probe 122. The dispenser 109 is preferably located in zone 150. Liquid applied to the probe 122 through the dispenser 109 preferably is collected in a drain or in a re-circulation basin (not shown). The liquid applied through the dispenser 109 can be either de-ionized water, or one of many known chemical treatments, such as an ammonia peroxide mixture. The dispenser 109 can be used to dampen the megasonic energy in the probe 122. This technique is referred to as "loading" the probe. The probe 122 is preferably loaded by applying liquid to it from the dispenser 109 at a radial position between the edge of the substrate and the inner wall of the process bowl 106. The cleaning apparatus 100 preferably has control systems capable of either loading or not loading the probe, as required. Loading the probe draws some of the megasonic energy out of the probe and directs it away from the surface of the substrate 114. This may improve the cleaning because some devices formed on the surface of the substrate 114 may be too sensitive to clean without dampening. The application of liquid from the dispenser 109 can reduce damage to such devices while still enabling cleaning for some applications. This technique can be used in combination with other techniques, such as changing the applied power, frequency, and energy directivity of the probe, to control damage. By applying liquid to the probe from the dispenser 109, the throughput of the substrate cleaning process can also be reduced because the time required for the probe 122 to contact the liquid on the surface of the substrate can be reduced.

The dispenser 109 in the apparatus 100 provides several advantages. One advantage related to the probe dampening described above involves tuning the probe 122. Each probe has slightly different cleaning performance. As a result, prior to installing the probe into the apparatus 100, the probe 122 preferably is tuned. Furthermore, a specific substrate type used by a customer may be very sensitive to the energy applied to it, and, as a result, too much energy could cause damage to that type of substrate. Accordingly, the probe 122 may need to be tuned to the customer's substrate type. Probe tuning involves operating the probe at a variety of frequency to find the frequency that provides the best cleaning performance. Sometimes, however, adjusting the frequency of the power applied to the probe 122 does not provide enough tuning resolution, i.e., adjacent frequency steps are too large to produce the desired cleaning performance. In that case, the probe dampening technique described above can be used in combination with frequency adjustments to properly tune the probe.

As mentioned above, it is desirable to reduce throughput for cleaning substrates on the apparatus 100. As discussed in more detail below, in connection with FIG. 20, the probe is extendable into and retractable out of the bowl 106. The dispenser 109 advantageously improves throughput by enabling the probe 122 to apply megasonic energy to the substrate while it is being extended over the substrate. By applying liquid to the probe 122 from the dispenser 109, the amount of power transmitted through the meniscus can be scaled to prevent damage to delicate structures on the surface, to account for the lower area of contact between the probe and the liquid, or to otherwise scale the effective power as needed. This improves cleaning efficiency, cleaning throughput, and, therefore, the cost of ownership associated with the apparatus 100.

Another advantage provided by adding the dispenser 109 is that liquid from the dispenser 109 can be used to rinse the probe 122. By rinsing the probe 122, contaminants picked up by the probe 122 during the cleaning of a prior substrate 114 can be reduced prior to the cleaning of a subsequent substrate 114. By reducing contaminants on the probe 122, cleaning of the subsequent substrate 114 by the apparatus 100 will be more effective and more efficient.

The meniscus may further be controlled by carefully controlling the fluid flow properties of the cleaning media directed at the substrate 114 by the nozzles of the dispensers 108. These properties are controlled by selecting a preferred nozzle inner diameter. Varying the nozzle diameter affects the fluid flow of the cleaning media. For example, for a cleaning liquid supplied to the nozzle at a constant pressure, smaller nozzles tend to produce higher cleaning fluid velocities. The preferred fluid pressure for cleaning liquid supplied to the nozzle is in a range between about 2 and about 30 pounds per square inch, or between about 13,700 newton per square meter and about 206,800 newton per square meter. Higher fluid velocities tend to interfere more with the cleaning capability of the probe. Thus, the nozzle size preferably is controlled. In order to clean adequately, the nozzle size is preferably greater than about 0.125 inches, or about 3.2 millimeters, in one embodiment. The cleaning media dispenser nozzle size is preferably greater than about 0.25 inches, or about 6.4 millimeters, in another embodiment. The cleaning media dispenser nozzle size is most preferably about 0.25 inches, or about 6.4 millimeters.

As mentioned, the flow velocity of the liquid exiting the nozzle increases with smaller nozzle sizes for the same volumetric flow rate. Because the distance between the nozzle and the substrate is fixed, varying the nozzle size may require that the trajectory of the liquid be varied. Thus, for a 0.125 inch nozzle, the trajectory of the nozzle and the liquid as it initially exits the nozzle is approximately fifteen degrees below the horizon. By contrast, for a 0.25 inch nozzle, the trajectory of the nozzle and initial trajectory of the liquid is between about thirty degrees and about forty-five degrees above the horizon, see FIG. 3B.

Another variable which can increase cleaning efficiency is the capability to pulse the application of cleaning media to the substrate. This pulsing preferably involves turning the dispensing nozzle on and off at regular intervals. More generally, it could involve varying the volumetric flow rate of the media exiting the dispenser. For a given dispenser geometry, and for liquid cleaning medium, the flow velocity is adjusted by varying the fluid pressure. Thus, the dispensers preferably can be controlled to apply liquid to the substrate in a pulsing manner. In the pulsing mode, the cleaning media dispensing nozzles preferably are cycled at a frequency between 0.1 hertz and 0.5 hertz, i.e., a period ranging from 2 seconds to 10 seconds. Alternately, the fluid pressure could be varied between, for example, between about 30 pounds per square inch, or about 206,900 newton per square meter, and about 2 pounds per square inch, or about 13,700 newton per square meter. More preferably, the pressure could be varied between about 10 pounds per square inch, or about 69,000 newton per square meter, and about 2 pounds per square inch, or 13,700 newton per square meter. Pulsing could be achieved using other techniques. For example, pulsing application of fluid to the substrate could also be achieved by varying the fluid flow rate between the preferred maximum flow rate and a lesser, non-zero flow rate.

Other variables which can be used to control the manner in which acoustic energy propagates through the meniscus include the height of the meniscus, the frequency of the energy applied to the probe, and other factors. As discussed above, the frequency applied to the probe 122 can be adjusted in order to tune the probe 122. This process yields a preferred operating frequency for the probe 122 that might correspond to the highest cleaning efficiency. The probe 122 can operate at a wide range of frequencies, for example, between about 500 kilohertz ("kHz") and about 1.5 megahertz (MHz). The probe 122 can also operate very well in a frequency range between about 825 kHz and about 850 kHz. The probe 122 can also operate very well within a frequency range from about 836 kHz to about 844 kHz. The probe 122 can operate very well at about 836 kHz or about 844 kHz. As discussed below in more detail, the apparatus 100 further comprises a controller 147, which is programmable to apply megasonic energy to the probe at one or more of the frequency ranges described above.

As discussed above, the preferred operating frequency of an individual probe 122 can depend on several factors, for example, the actual dimensions of the probe 122, the overall dimensions of the entire cleaning assembly 118, the substrate application and other factors. As discussed above in connection with loading the probe 122, when the cleaning application involves substrates 114 carrying very delicate structures, the preferred operational frequency of megasonic energy applied to the probe 122 can be altered from the frequency corresponding to the highest cleaning efficiency. This other frequency can reduce the possibility of the probe 122 damaging delicate structures on the substrate 114.

Figure 4A:
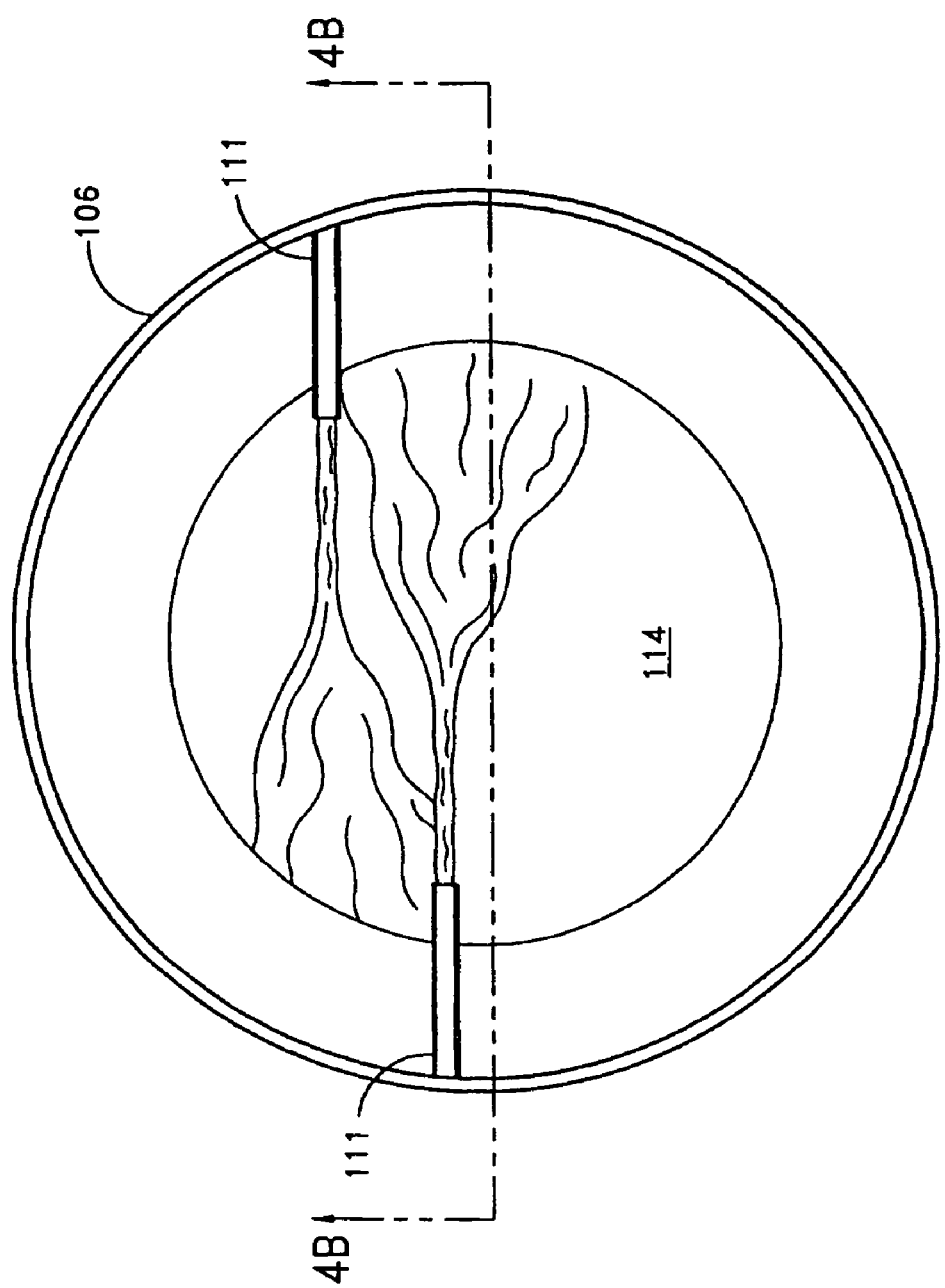
FIG. 4A is a schematic top view of the multi-dispenser rinsing configuration of FIG. 1.
Figure 4B:
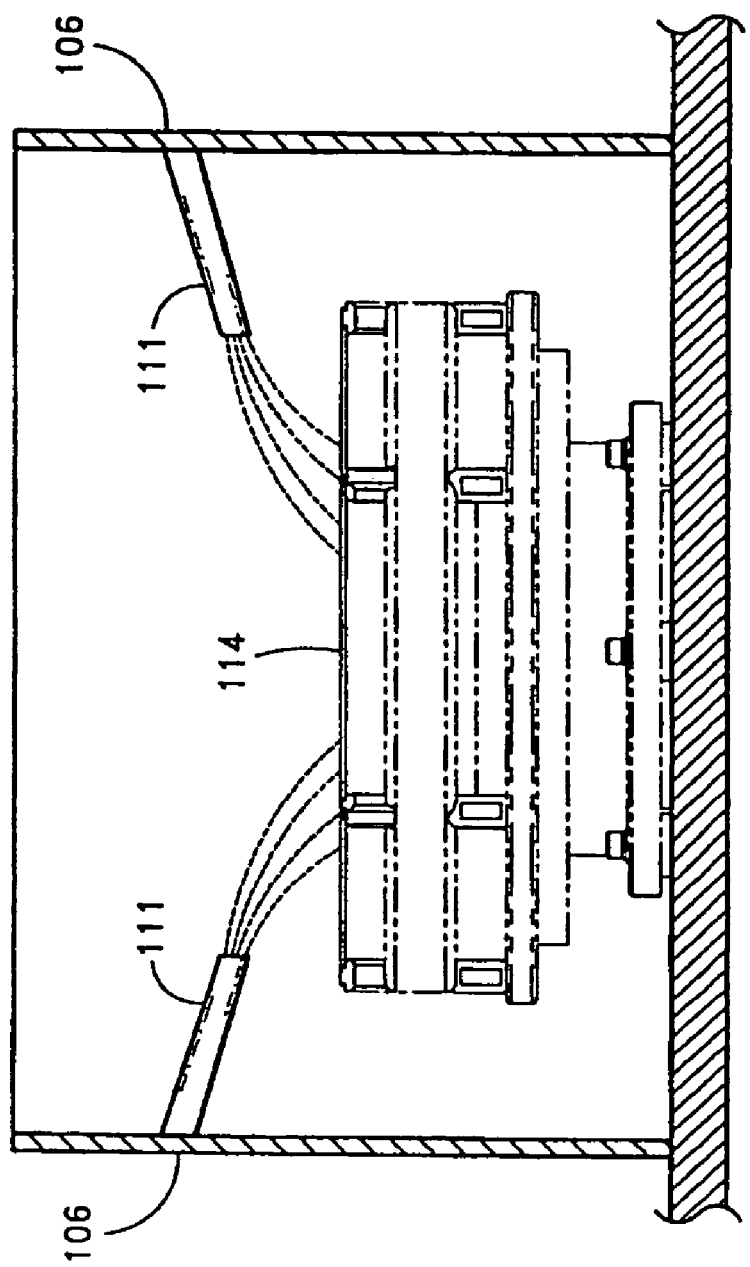
FIG. 4B is a schematic side view of a multi-dispenser rinsing configuration of the cleaning apparatus of FIG. 4A.
Figure 5:
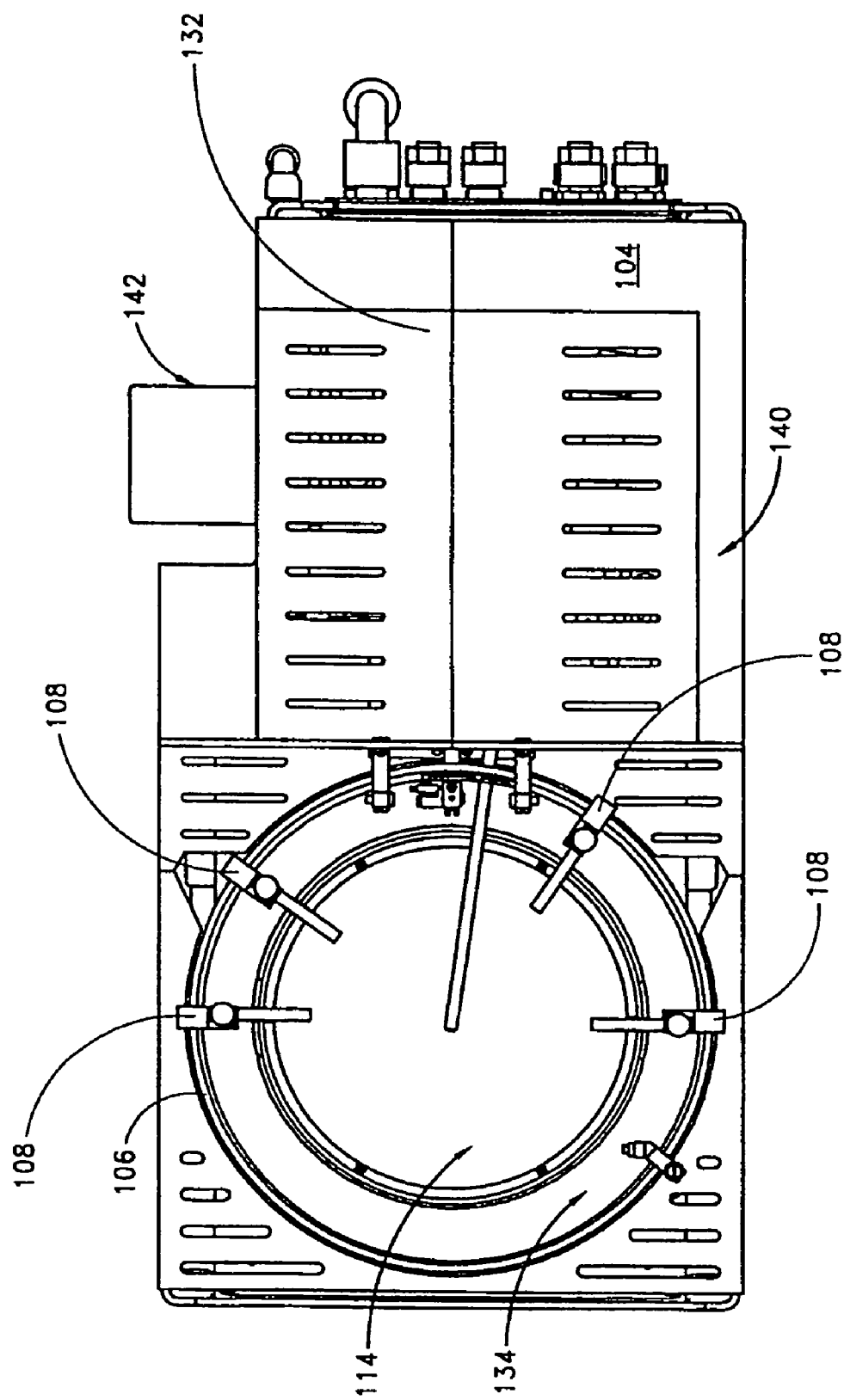
FIG. 5 is a top view of one embodiment of the substrate cleaning apparatus.

FIGS. 4A and 4B illustrate another embodiment of the apparatus 100. It may sometimes be desirable to apply a rinse to the substrate 114, in addition to the cleaning and drying. While the rinsing step can add to the throughput, a multi-dispenser rinsing configuration can minimize the additional processing time. As shown in FIG. 4A, a plurality of rinsing dispensers 111 are mounted to the process bowl 106 and are configured to apply rinsing liquid to the substrate 114. During the rinse, there generally is no need to maintain a controlled meniscus. Therefore, a high velocity rinsing process can be used. As shown in FIG. 4B, the rinsing dispensers 111 in the high velocity rinsing process may be oriented downwardly with respect to the horizon, for example, by about fifteen degrees. The two rinsing dispensers 111 advantageously approximately doubles the volume of rinsing liquid that is applied to the outer edge of the substrate 114 compared to a single rinse dispenser configuration for each revolution of the substrate. This decreases rinsing process time, where needed, and therefore minimizes throughput of processes that require rinsing. The rinsing dispensers 111 could also be positioned on the bowl 106 to dispense onto the center of the substrate 114.

The probe 122 is extendable into and retractable out of the bowl 106 through one of the apertures in the side wall of the bowl 106. For example, as shown by the arrow 124, the assembly 118 is movable in a radial direction. The assembly 118 preferably may be extended outward from the rear-most side wall of the process bowl 106 until it reaches about the center or just beyond the center of the substrate 114. On the other hand, when the assembly 118 is retracted, most of the probe 122 is received beneath the cover 132. As described in the above-noted U.S. Pat. No. 6,140,744, megasonic energy applied to a transducer coupled to the probe 122 propagates through the probe 122, and through the meniscus of liquid onto the substrate 114 to loosen particles on the substrate 114 while the substrate 114 is rotating.

In the preferred embodiment, the process bowl 106 also comprises a second aperture for receiving drying assembly 120. The assembly 120 may include a drying head 128, which is described in greater detail in European Patent application publication EP0905747A1. As described therein, the drying assembly 120 has a substrate drying assembly support arm 130 mounted to be moveable radially with respect to the substrate 114 into and out of a position closely spaced above the upper surface (the device side) of the substrate 114 supported on the chuck 110. The drying assembly 120 includes an outlet that applies, or dispenses, liquid to the surface of the substrate and also includes an outlet that applies, or dispenses, tensioactive vapor to the surface of the substrate 114. The drying vapor outlet is positioned radially beyond the drying liquid outlet. The drying assembly 120 is designed to be extendable through the rear-most side wall of the process bowl 106 toward and just beyond the center of the processing chamber of the process bowl 106. The drying assembly 120 also resides primarily under the cover 132 when retracted. The operation of the drying assembly 120 and the cleaning assembly 118 can be carefully controlled in order to sufficiently clean the substrate 114 at a satisfactory speed. This control is described in connection with a method described below. The drying assembly 120 dries the surface of the substrate 114 through centrifugal action and by displacing the processing liquids on the surface with a tensioactive liquid that reduces the surface tension of the processing liquids.

A moveable splash guard 134 is also located in the process bowl 106, and is discussed in greater detail with respect to FIGS. 11A–13. In the preferred embodiment, the movement of splash guard 134 is generated by a plurality of supports that comprise front support 136 and rear supports 138. As shown in FIG. 1, the support 136 extends through the decktop 104, while the supports 138 extends through the rear cover 132. Of course it will be understood that the support locations may be varied affecting the operation of the splash guard 134.

Referring now to FIG. 2, a valve manifold and associated piping 140 is provided to supply the liquid and/or gas which is dispensed by the dispensers 108. The dispensers 108 each comprise an outlet for directing the liquid and/or gas onto the surface of the substrate 114 at a preferred location. The piping 140 resides beneath the cover 132. The cleaning apparatus 100 also comprises an exhaust and drain manifold 142 to carry away waste gases, liquids and contaminants.

FIG. 6 shows a portion of the removable decktop 104 cut away. A main reference plate 163 can be seen beneath the decktop 104. The megasonic probe 122, which is positioned at an elevation above the substrate 114 when the substrate 114 is positioned within the substrate chuck 110, is actuated by a megasonic probe drive module 144. The drying head 128, also positioned at an elevation above the substrate 114, similarly is actuated by a drying assembly drive module 146. Both drive modules 144, 146 are mounted within the cover 132 on the assembly main support plate 163, are controlled by a controller 147, and are discussed in greater detail below in connection with FIGS. 15–16. In the illustrated embodiment, both drive modules 144, 146 are linear drive modules, but any suitable drive profile will work.

Referring now to FIGS. 7–8, the substrate chuck assembly 112 comprises a servomotor 160 and a substrate chuck bearing cassette 162, each having a pulley mounted thereon and each being mounted to the support plate 163. The pulley of the motor 160 and the pulley of the cassette 162 are connected by a timing pulley drive belt 164. The substrate chuck bearing cassette 162 has a tubular, or open-center, shaft 166 providing an area 168 that can contain dispensers, sensors and other components. In some embodiments, the area 168 is a dispensing area through which cleaning fluid can be directed to apply fluid to a lower surface of the substrate. Although described herein as a bearing cassette, any suitable bearing that will work with the tubular shaft 166 can be used.

The tubular shaft 166 provides access for tubing, wiring, mechanical components and the like 170 which may perform cleaning of the bottom side of the substrate 114. For example, a bottom-side fluid dispenser 171 can extend upwardly through the tubular shaft 166 into a position to be able to apply liquid to the bottom surface of the substrate 114 (see FIG. 9B). FIG. 9B shows that the bottom-side fluid dispenser 171 can provide unobstructed access for fluid directed through the bottom-side fluid dispenser 171. The dispenser 171 is shown schematically in FIG. 9B with no mounting hardware. There are many ways that the dispenser 171 could be mounted so that it can deliver cleaning media to the substrate surface. For example, the dispenser 171 could be held in place by a bracket 173 mounted on the support plate 163. This bracket could be generally in a "J" shape, with the upstanding portion of the "J" extending into the open center shaft and with the two upstanding portions straddling the pulley attached to the inner race of the bearing cassette (see FIGS. 7–8). The plurality of dispensers 108 mounted at an elevation higher than the substrate 114, meanwhile, are able to apply liquid to the top surface of the substrate 114. In this way, the apparatus 100 can perform simultaneous cleaning of both sides of the substrate 114.

As shown in FIG. 9B, the substrate chuck 110 has a lower support 172, which is a horizontally extending portion, that is secured to an upper end of the tubular shaft 166 of the bearing cassette 162 with a plurality of chuck mounting fasteners-174. The bearing cassette 162 is also connected to the substrate chuck 110 in a manner that permits the chuck 110 to rotate with respect to the plate 163. The tubular shaft 166 preferably has a four inch diameter, or about a 102 millimeter diameter.

When the motor 160 is driven in a controlled manner, the rotation of the motor 160 is transferred through the belt 164 to the cassette 162 causing the cassette 162 and the substrate chuck 110 to also rotate in a controlled manner. The substrate chuck 110 also comprises a plurality of substrate support posts 176. The posts 176 extend upwardly from an upper surface of the horizontal portion, or lower portion, 172. The posts 176 are described in more detail below. In the preferred embodiment, the substrate chuck 110 is fixed in the direction perpendicular to the surface of the plate 163, vertically fixed in the arrangement shown. Other substrate chucks configured to telescope (i.e. to be movable in the direction of the axis of rotation) are known could be implemented in this substrate cleaning system as well.

As shown in FIG. 9B, the substrate chuck 110 supports the substrate 114 above the bearing cassette 162. The substrate 114 is positioned at an elevation above the bearing cassette 162 by the plurality of substrate support posts 176. As may be seen, the support posts are reinforced by a band 177 connecting each of the support posts 176 about half the distance up the posts 176. The band 177 prevents the posts 176 from flexing in operation so that the posts 176 continue to support the substrate 114 throughout the cleaning and the drying processes. There is an open space between the band 177 and the base of the chuck 110 which permits liquid beneath the substrate to escape out the side of the chuck.

By so supporting the substrate 114, a space is created underneath the substrate 114 which may be accessed by the various components 170. The substrate support posts 176 provide a passive restraint of the substrate 114. The passive restraint may comprise a notch which is located on the side of the post closest to the axis of a rotation of the bearing cassette 162. This notch comprises a horizontal portion and a vertical portion. The horizontal portion provides a surface upon which the substrate 114 rests. Therefore, the horizontal portion of the support post 176 provides a passive restraint in the vertical direction against the force of gravity. The vertical portion provides a surface upon which the outer edge of the substrate 114 may be pressed by the rotation of the substrate chuck 110. Therefore, the vertical portion of the support post 176 provides a passive restraint in the form of centripetal force in the horizontal direction. Of course other devices could be used to hold the substrate in position, such as a mechanism actuated by the rotation of the chuck 110. Such a mechanism would press against the substrate to hold it in place when the substrate is rotating, but release it when it is not.

Figure 10:
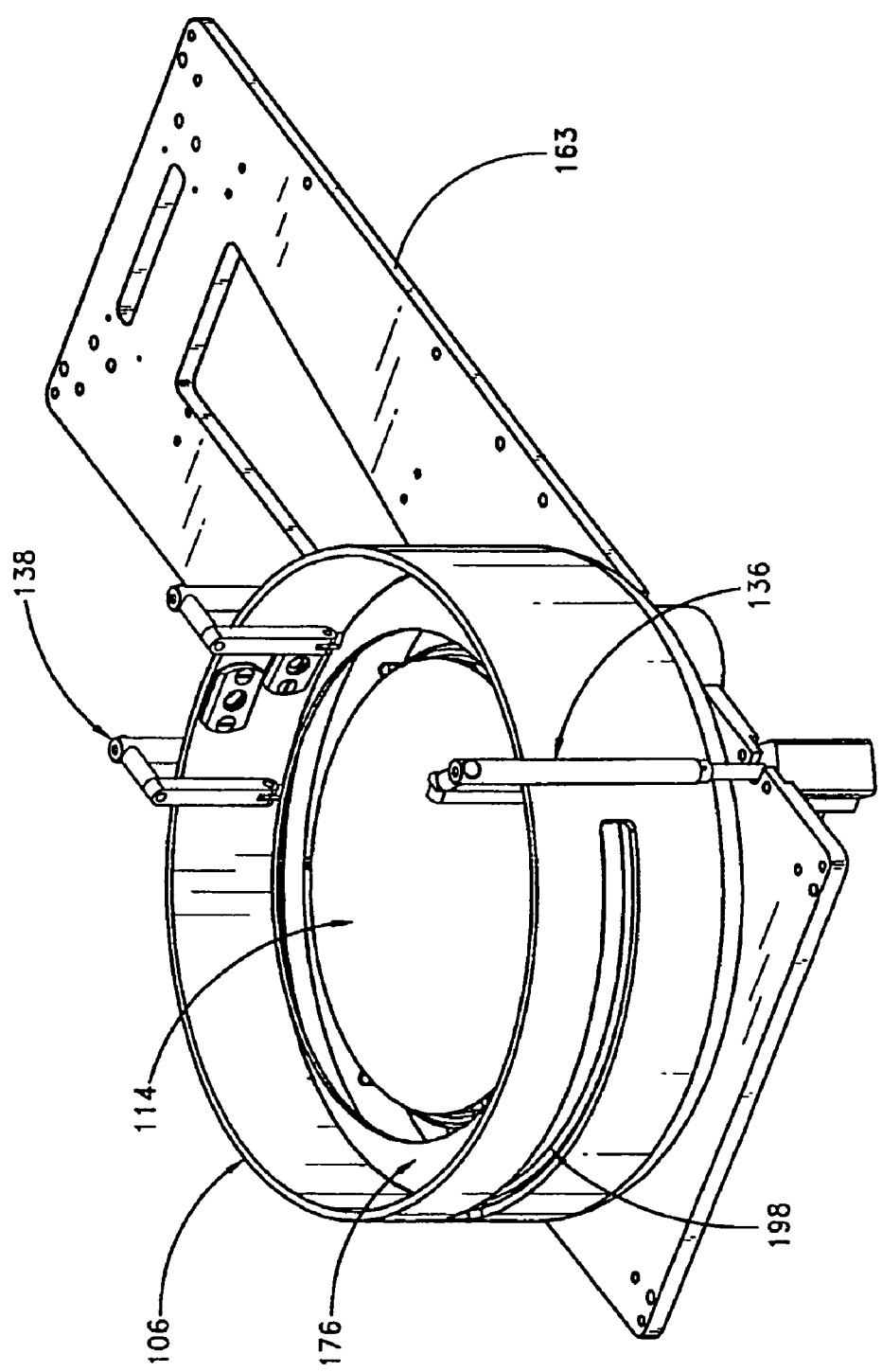
FIG. 10 is an isometric view of one embodiment of the process bowl of one embodiment of the substrate cleaning apparatus.

Referring to FIG. 10, the process bowl 106 is shown with the cleaning components removed. The process bowl 106 is mounted on support plate 163 and has a load/unload access slot 198 to receive a robot arm. The slot 198 is located on the front side of the bowl 106 and is at least as wide as the diameter of the substrate 114. The height of the slot is sufficient to allow robotic loading and unloading of the substrate 114 onto the substrate chuck 110. Therefore, the top of the slot 198 must be at an elevation that is higher than the top of the substrate support post 176 by at least the thickness of the substrate 114. The bottom of the slot 198 is at an elevation that is at least below the horizontal portion of the notch by an amount of the thickness of the robot arm. The robot arm preferably has a paddle configured to extend into the open center of the chuck 110 during the process of loading or unloading the substrate onto the chuck 110. The paddle extends beneath the substrate 114 but above the band 177.

Also mounted to the support plate 163 are the supports 136, 138 supporting the moveable splash guard 134. The supports 136, 138 are vertically actuatable and as they are raised, the splash guard 134 correspondingly also is raised relative to the fixed elevation of the substrate 114 when positioned on the substrate chuck 110. As shown, the supports 136, 138 may comprise one or more hinges 139 to facilitate the movement of the splash guard 134. Of course other numbers of moveable supports could also be used to move the splash guard 134.

Figure 11A:
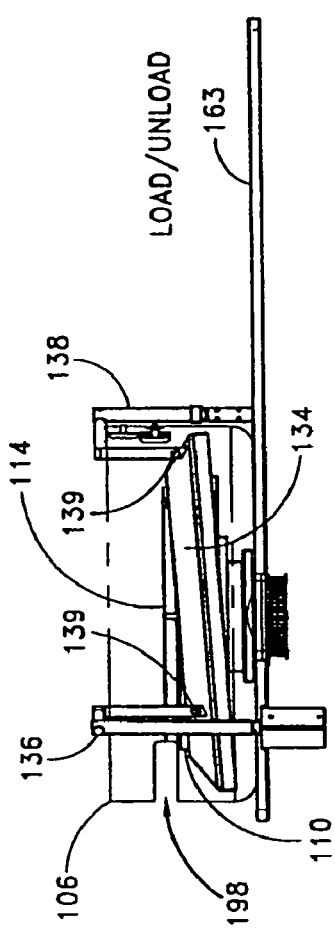
FIGS. 11A–11C are side elevation views of one embodiment of the moveable splash guard in various process positions with the process bowl shown in phantom.
Figure 11B:
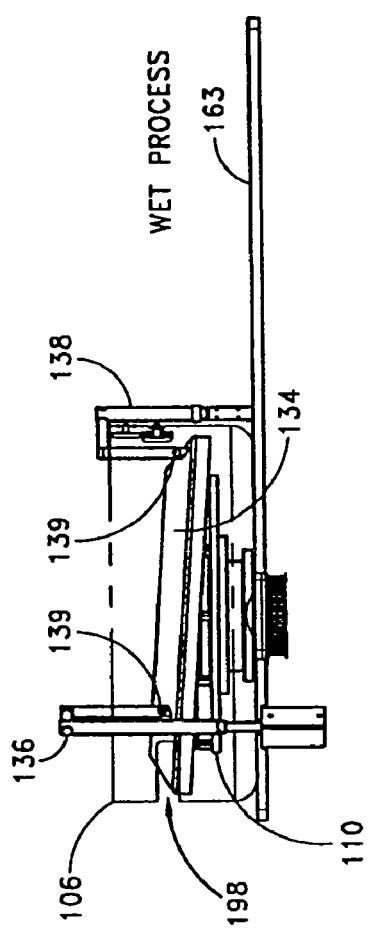
Figure 11C:
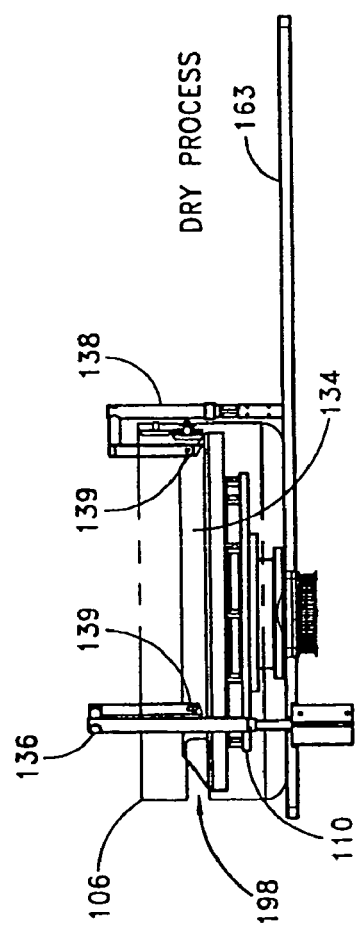

Referring now to FIGS. 11A–11C, the supports 136, 138 are vertically moveable so as to position the moveable splash guard 134 appropriately with respect to the slot 198 and with respect to the substrate 114 when it is positioned on the chuck 110.

Referring to FIG. 11A, the supports 136, 138 are moveable such that the front of the moveable splash guard 134 is disposed at an elevation below the slot 198. This may be termed the retracted position, or the substrate load/unload position. When the splash guard 134 is in the retracted position, a robot arm delivering the substrate 114 into the processing chamber can be extended through the slot 198 until the substrate 114 is directly above the substrate chuck 110. Then the robot arm can lower the substrate 114 onto the chuck 110. This is referred to herein as loading the substrate onto the substrate support, or chuck. As described above, the slot 198 is tall enough so that the robot arm can be lowered to an elevation below the horizontal portion of the notch in the support posts 176. At this lower position, the robot arm can be withdrawn from the processing chamber without touching the substrate 114. The retracted position of the splash guard 134 thus facilitates loading and unloading using a robot arm.

Referring to FIG. 11B, the moveable splash guard 134 can also be positioned by actuating the supports 136, 138 into a wet processing position. In the wet processing position, the front side of the splash guard 134 is disposed at an elevation higher than the rear side of the splash guard 134. The elevation of the top of the splash guard 134 is above the front side of the substrate 114 and is just low enough near the rear side to provide access to the substrate 114 for the cleaning probe 122. There is also just enough clearance in this position for the liquid and vapor outlets of the drying head 128 to be extended out over the substrate 114. In this position, the splash guard 134 contains the processing liquids, preventing them from escaping through the slot 198. At the rear side of the substrate 114, a small portion of the substrate 114 may be at or just above the elevation of the splash guard 134. This prevents all but a very small amount of liquid from being flung over the top of the splash guard 134. Floating seals surround the probe 122 and drying head 128 to contain this small amount of liquid. Also, the bottom of the splash guard 134 is at an elevation below the bottom of the slot 198.

Finally, referring to FIG. 11C, the supports 136, 138 can be actuated to move the moveable splash guard 134 into a dry process position in which the drying head 128 is extended out over the top surface of the substrate 114. In this position, the splash guard 134 is brought to a generally horizontal position, i.e. the perpendicular distance from the substrate 114 to the plane of the top of the splash guard 134 is a constant value. In the dry process position, the top of the splash guard 134 is at an elevation above the slot 198 and the bottom of the splash guard 134 is at an elevation below the bottom of the slot 198. This prevents any liquid which is flung off the substrate from exiting the apparatus 100 into the surrounding area. The splash guard 134 also deflects processing liquids away from the substrate surfaces to prevent splash-back onto the surface of the substrates.

Referring to FIG. 12, the moveable splash guard 134 comprises a cylindrical band 210 with an annular surface having a diameter greater than the diameter of the substrate chuck 110 but less than the diameter of the process bowl 106 (see FIG. 1). Connected to the top portion of the cylindrical band 210 is a frusto-conical portion 212 disposed at an angle $\alpha$ with respect to the plane of the base of the splash guard 134. The inner diameter of the conical portion 212 is greater than the outer diameter of the substrate chuck 110. The annular surface of the frusto-conical portion 112 that faces the substrate 114 is preferably smooth. Other surfaces may also be effective, however, such as the mesh-type splash guard described in connection with FIG. 14 below.

As may be seen in FIG. 12, liquid on the surface of the substrate 114 is projected off the substrate 114 towards the annular surface of the conical portion 212 of the moveable splash guard 134 by centrifugal force arising from the spinning of the substrate 114. This liquid strikes the annular surface of the conical portion 212 at the angle $\alpha$ and is deflected by the annular surface of the conical portion 212 of the moveable splash guard 134 in a direction that is generally downward but also radially outward from the outer edge of the substrate 114. The angle $\alpha$ is between 10 degrees and 60 degrees in one embodiment. The angle $\alpha$ is between 20 degrees and 50 degrees in another embodiment. The angle $\alpha$ is between 30 degrees and 40 degrees in another embodiment. The smoothness of the annular surface of the conical portion 212 tends to preserve the droplets rather than causing them to vaporize. As mentioned above, and discussed in more detail in connection with FIG. 14, other splash guard surface configurations can also prevent splash-back onto the substrate 114.

Figure 13:
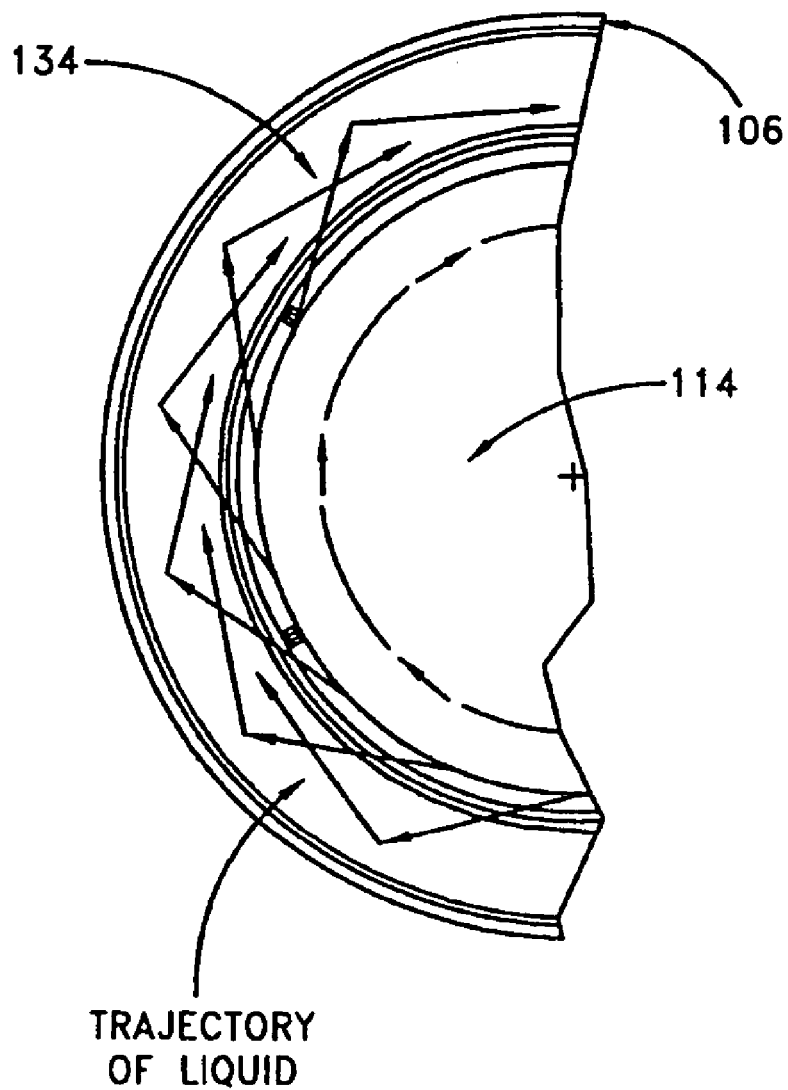
FIG. 13 is a partial top view of one embodiment of the processing chamber of the substrate cleaning apparatus showing the trajectory of cleaning liquids.

FIG. 13 further illustrates the trajectory of the liquid which is transported off the surface of the substrate 114 by the centrifugal force exerted on the liquid on the surface of the spinning substrate 114. The trajectory of the transported liquid is generally in the direction of the rotation of the substrate 114. As the liquid moves off the substrate it travels toward the annular surface of the conical portion 212, strikes the annular surface and is deflected at an angle away from its original path between the substrate 114 and the annular surface. The liquid is deflected in such a manner as to prevent the liquid from splashing back onto the substrate 114. Splash-back of liquid can be prevented by positioning the annular surface at an angle, as described above, so that the liquid is deflected downward relative to the elevation of the surface of the substrate and outward radially from the center of the chuck 110. As mentioned above, the drying process works by displacing the cleaning liquids on the substrate surface with surface tension reducing liquid. The moveable splash guard 134 is used in conjunction with the drying assembly 120 to assure little or no drying through evaporation from the substrate surface of splash-back of cleaning liquid occurs.

Figure 14:
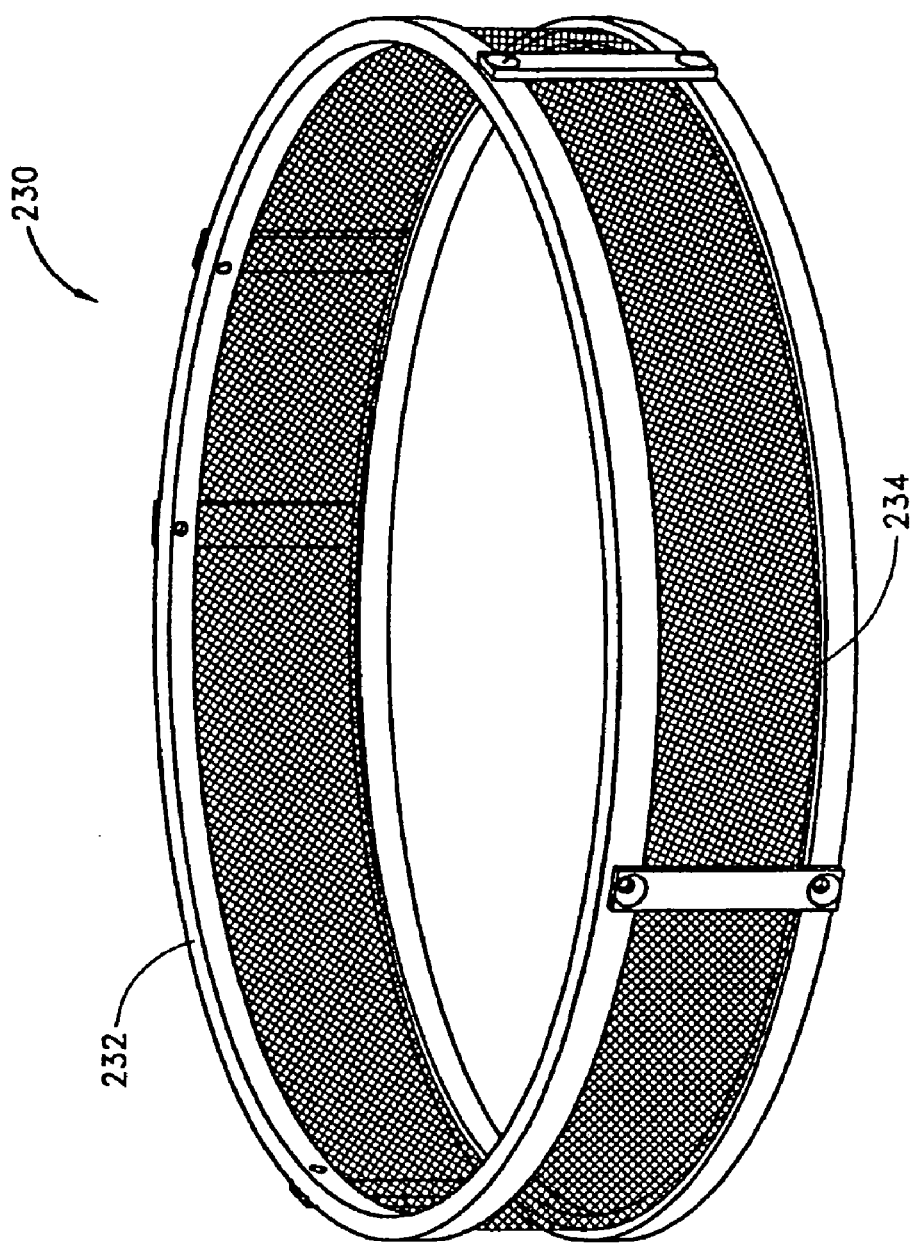
FIG. 14 is an isometric view of one embodiment of a mesh-type splash guard.

Referring now to FIG. 14, a mesh-type splash guard 230 is shown. The mesh-type splash guard 230 comprises a frame 232 and a mesh portion 234. The mesh portion 234 preferably comprises a plurality of strands arranged in a crossing fashion (e.g. perpendicularly crossing) to form a grid of rectangular openings. More generally, two sets of strands may form any quadrilateral shape. Also, more than two sets of strands may be used to form the mesh with openings of any polygon shape. In one variation, the mesh has about a 1 mm aperture with about a 44 percent open area. The mesh portion 234 may be affixed to the frame 232 or the frame and mesh may be unitary. Although shown as a cylinder, the mesh-type splash guard 230 may have a variety of shapes, and may, for example, be formed as a frusto-conical portion, like the splash guard 134.

Another variation comprises a splash guard having at least two mesh sections. In this arrangement, a second mesh section is positioned generally concentrically around a first mesh section. Generally, the first mesh section will have apertures and open area equal to or larger than the apertures and open areas of the second mesh. The second mesh can have about a 1 mm aperture with about a 44 percent open area. In another variation, the second mesh can have about a 0.3 mm aperture with a 36 percent open area. In still another variation, the first mesh section can have about a 1 mm aperture with about a 44 percent open area and the second mesh can have about a 0.3 mm aperture with about a 36 percent open area. Yet another variation involves using a mesh portion similar to mesh portion 234 in conjunction with an annular splash guard similar to the guard 134.

As with the splash guard 134, the splash guard 230 may be attached to supports 136 and 138 that are vertically actuatable. Together with the hinges 139, the supports 136, 138 permit the mesh-type splash guard 230 to be moved as the splash guard 134 is moved, as shown in FIGS. 11A–11C. Like the conical portion 212, the mesh portion 234 of the mesh-type splash guard 230 intercepts the liquid being spun off of an upper surface of the substrate 114 in a manner that prevents the liquid from splashing back onto the upper surface of the substrate 114.

Figure 15:
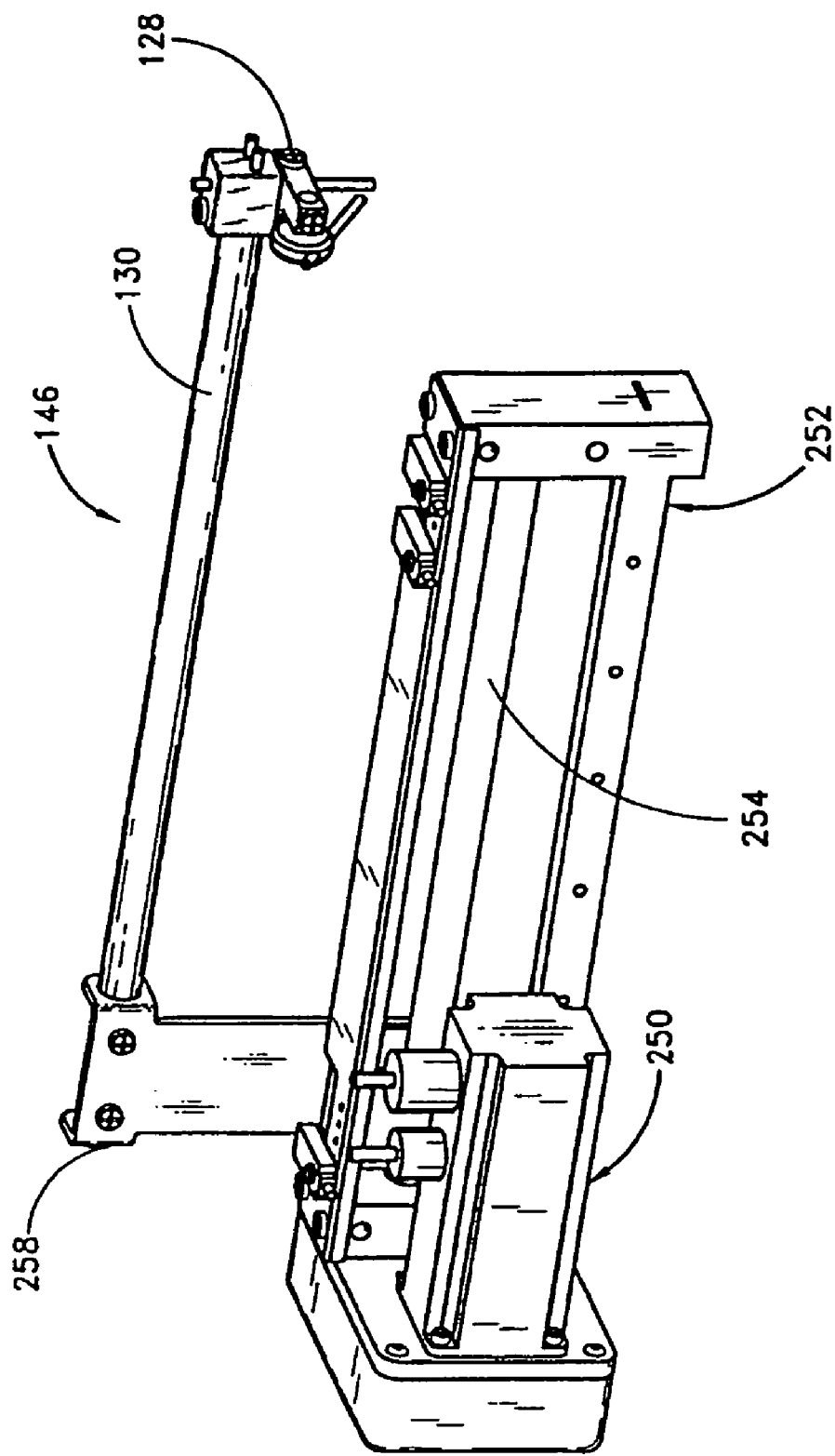
FIG. 15 shows a drive module in isometric view.
Figure 16:
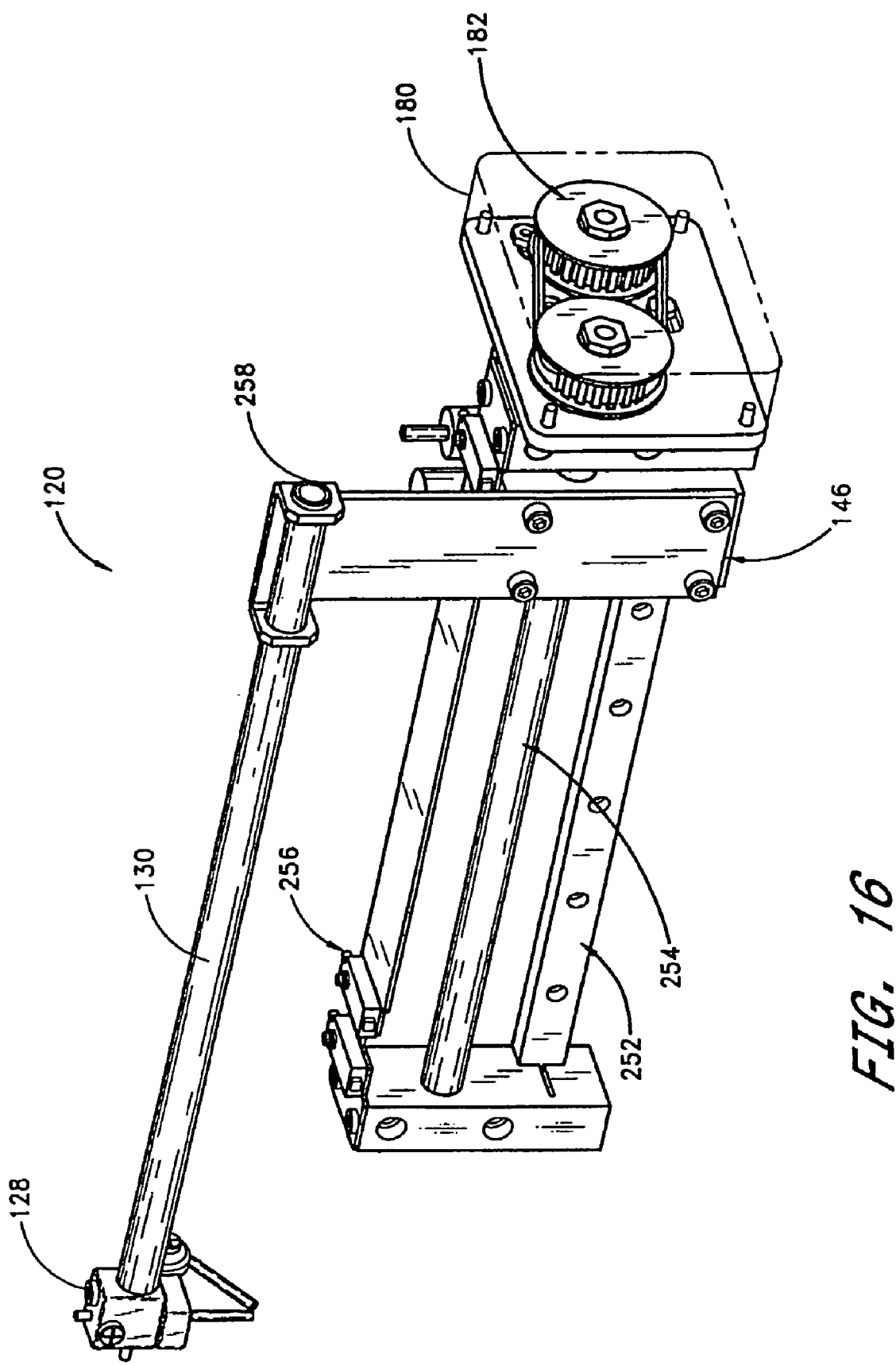
FIG. 16 shows an isometric view of one embodiment of the drive module for a substrate drying assembly.

Referring now to FIGS. 6, 15, and 16, the cleaning and drying apparatus 100 comprises a drying assembly drive module 146. In the preferred embodiment, the drive module 146 comprises a servomotor 250, a linear bearing 252, a lead-ballscrew 254, and a proximity sensor 256 for sensing a limit position and a home position. The drying assembly 120, which includes the drying head 128 and the substrate drying assembly support arm 130, is mounted onto the drive module 146 with a bracket 258.

FIG. 16 shows all the components of the drive module 146 shown in FIG. 15, and further shows the drive mechanism housing 180 in phantom revealing the timing belt and pulley drive assembly 182. Although the cleaning assembly drive module 144 is not shown in detail, its construction is similar to the construction of the drive module 146, except the drying assembly 120 is replaced with the cleaning assembly 118.

The drive modules 144, 146 are driven by a controller 147 which positions the probe 122 or the drying head 128 radially with respect to the substrate 114. For example, the probe 122 is inserted or retracted radially from the processing chamber of the process bowl 106 by the drive module 144. The drive module 144 is connected to the cleaning assembly 118 and moves it radially with respect to the substrate 114 such that the end of the probe 122 extends toward or is retracted away from the center of the substrate 114. The drive module 144 also can retract the probe 122 so that it is outside of the outer diameter of the substrate 114. Similarly, the drive module 146 can extend the drying head 128 to a position at an elevation above the substrate 114 but within its radius and can also retract the cleaning head 128.

The controller 147 which actuates the drive modules 144, 146 can be used to implement various control strategies to maximize performance of the cleaning apparatus 100. Different control strategies may be selected depending upon many factors, for example, the size of the substrate, the cleaning solution used, the sensitivity of the structures being constructed on the surface of the substrate, and the degree of cleanliness required, among others. These control strategies can be illustrated graphically, for example on a two-dimensional graph.

Figure 17:
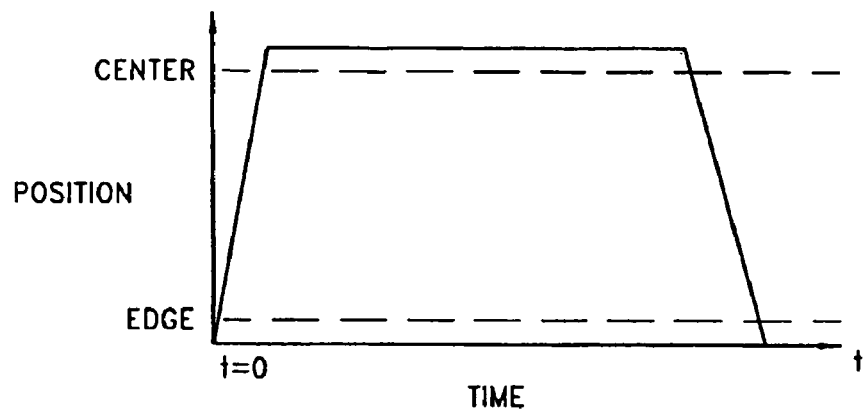
FIG. 17 shows a control strategy applied by the drive module for one processing method.

As shown in FIG. 17, the position of the probe 122 with respect to the substrate 114 can be illustrated over time. One way to illustrate this is to plot the position of the probe with respect to the edge or center of the substrate 114 on the y-axis and time on the x-axis. The position of the edge of the substrate 114 and the center of the substrate 114 are shown on the y-axis as dashed lines. The dashed line closer to the x-axis represents the edge of the substrate 114, while the dash line furthest from the x-axis represents the center of the substrate 114. The solid line in FIG. 17 represents the position of the probe 122 over time with respect to the substrate 114. The servomotor 250 extends the probe 122 in a generally radial direction at a constant linear velocity with respect to the bearing 252 until the probe tip is located at or just beyond the center of the substrate 114. Then, in one embodiment, the controller 147 stops the servomotor 250, making the linear velocity of probe 122 zero during the cleaning operation. In another embodiment, as discussed above in connection with FIGS. 2–3, liquid can be applied to the probe 122 to load the probe 122 while the probe 122 is being extended from the dispenser 109. In that case, the cleaning can take place while the probe 122 is being extended over the substrate 114. The probe 122 can also be loaded while it is stationary over the substrate 114 to lessen damage to structures on the substrate 114, to tune the probe 122, or for other reasons. At completion of the cleaning, the probe 122 is retracted at a constant linear velocity until it reaches the home position, which is radially farther from the center of the bearing cassette 162 than is the outer edge, or periphery, of the substrate 114. In another variation, megasonic energy can be applied to the probe 122 while it is being retracted. In that case, it may be necessary to load the probe 122 in order to apply the appropriate amount of megasonic energy to the surface of the substrate 114 while retracting the probe 122.

Figure 18:
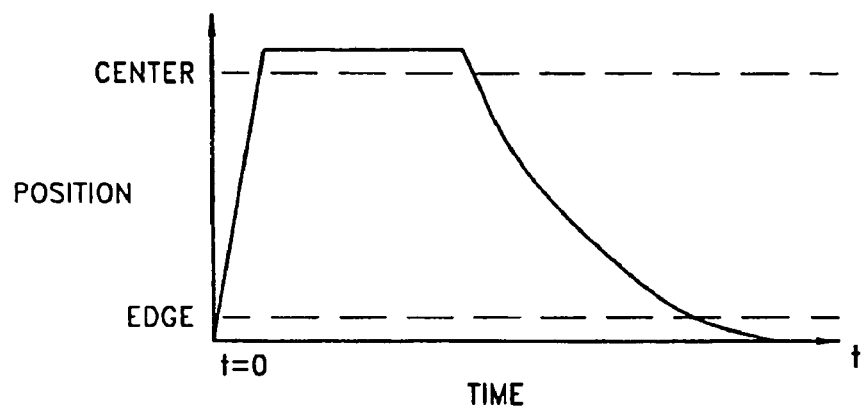
FIG. 18 shows a control strategy implemented by the drive module for another example processing method.

Another example control strategy is illustrated in FIG. 18, again in x-y coordinates, showing time and position respectively. The servomotor 250 extends the probe 122 in a generally radial direction at a constant velocity until the end of the probe 122 extends at or beyond the center of the substrate 114. Then, the controller 147 directs the servomotor 250 to stop, so the velocity of the probe is zero and the position of the probe 122 is held constant during the cleaning operation. Next, the controller 147 directs the servomotor 250 to retract the probe 122 at a varying velocity. That is, the linear velocity of the probe 122 with respect to the bearing 252 is greatest at the beginning of the retraction and the linear velocity of retraction is reduced continuously over the distance of travel of the probe 122 towards the edge of the substrate.

Figure 19:
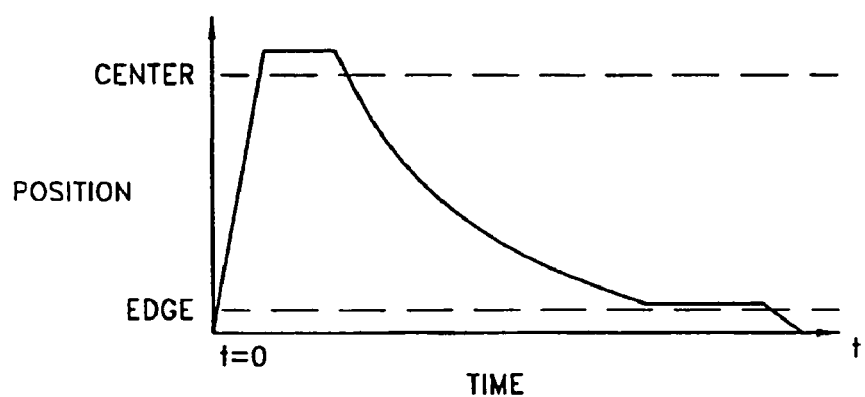
FIG. 19 shows a control strategy implemented by the drive module for another example processing method applied to the drying assembly.

Referring to FIG. 19, a control strategy for the drying assembly drive module 146 is illustrated. In this strategy the controller 147 directs the servomotor to extend the drying head 128 at a constant velocity from the edge of the substrate 114 to just beyond the center of the substrate 114. Then the controller 147 directs the servomotor 250 to stop, bringing the velocity of the drying head 128 at zero and holding its position constant for a period of time. Next, the controller 147 directs the servomotor 250 to retract the drying head 128 at a varying velocity, with the velocity of retraction being greatest at the beginning and with the velocity decreasing while the drying head 128 is moving toward the edge of the substrate 114. Next, the controller 147 directs the servomotor 250 to stop retracting the drying head 128 near the edge of the substrate 114, which brings the velocity of the drying head 128 to zero and holds its position constant for a period of time. Finally, the controller 147 directs the servomotor 250 to retract the drying head 128 at a constant velocity to return the drying head 128 to the home position.

Figure 20:
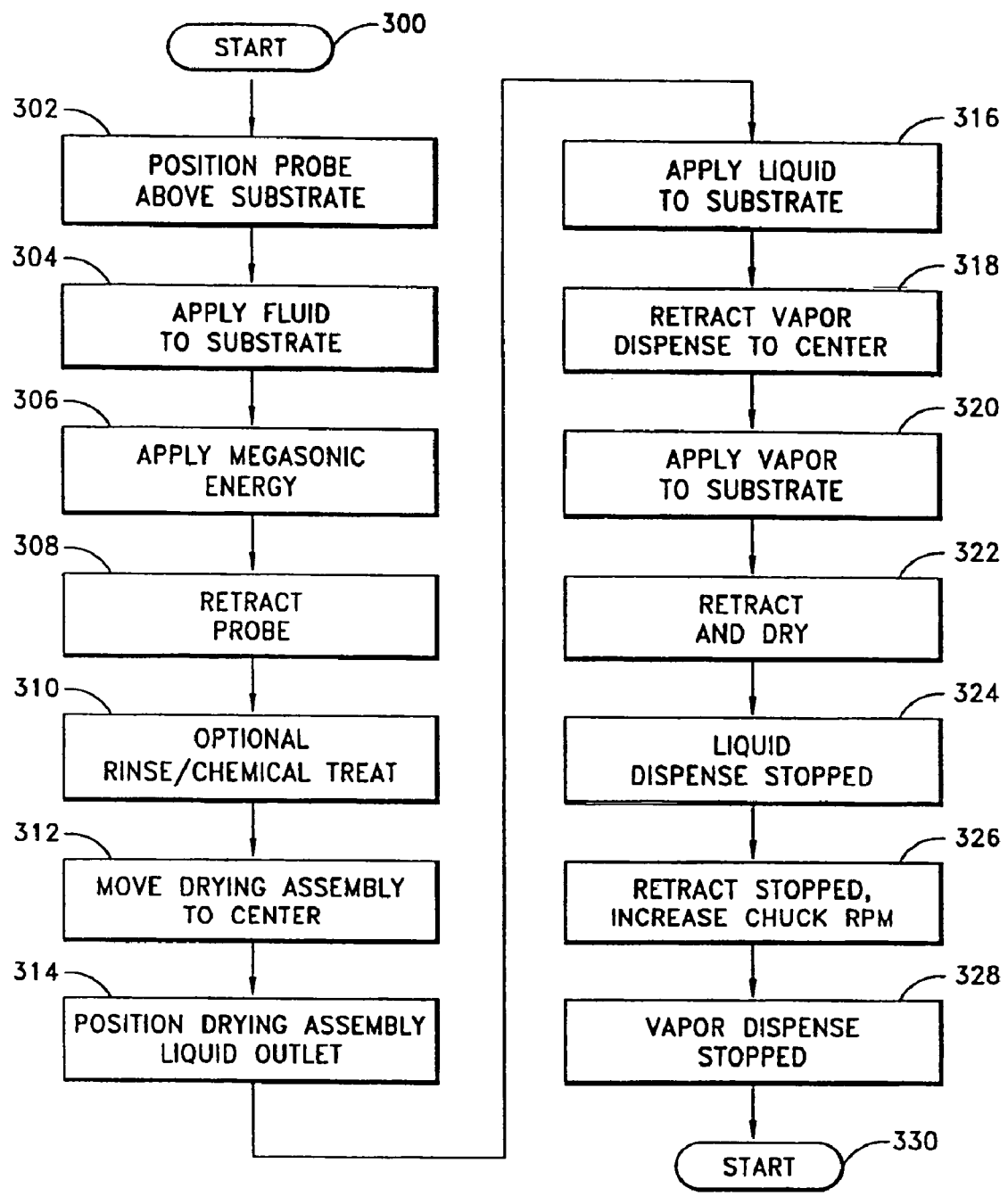
FIG. 20 shows a flow chart of one exemplary control strategy for cleaning and drying using the cleaning apparatus of the present invention.

The cleaning and drying apparatus 100 described above can be controlled to provide a satisfactory cleaning and drying process as illustrated by one preferred embodiment in FIG. 20. The process begins at a start block 300. Then, at a process block 302, the drive module 144 positions the probe 122 closely spaced above an upper surface of the substrate 114, which is positioned in and rotating with the chuck 110. Next at a process block 304, fluid is applied to the substrate 114 to create a meniscus between the probe 122 and the substrate 114. Then, in a process block 306 megasonic energy is applied to the probe 122 to cause it to propagate the megasonic energy through the meniscus to the substrate 114. The megasonic energy applied to the substrate 114 loosens particles on the substrate 114. The megasonic energy is strongest in the region of the probe 122. Therefore, it is preferred that the substrate 114 rotate beneath the probe at a first rate so that the entire upper surface of the substrate 114 is exposed to the megasonic energy. In one variation, the process steps 304 and 306 may be combined. In that case, megasonic energy is applied to the probe 122 as the probe is being extended over the substrate 114. This variation may further include applying liquid to the probe 122 through the dispenser 109 while the megasonic energy is being applied to the probe and while the probe is being extended over the substrate 114. Next in a process block 308 the probe 122 is retracted at or near the completion of a cleaning operation. In yet another variation, the process blocks 304, 306, and 308 could all be combined so that megasonic energy is applied to the surface of the substrate 114 through the probe 122 while the probe 122 is being extended, while it is stationary over the substrate surface, and while it is being retracted. In each of these stages, it may be desired to apply loading liquid to the probe 122 through the dispenser 109 to reduce the power applied to the surface of the substrate 114, to tune the probe 122, or for other reasons. Then, in a process block 310, the substrate 114 is rinsed with a suitable liquid. One preferred rinsing liquid is de-ionized water. In another variation, the process block 310 could include a chemical treatment, such as a treatment with hydrofluoric acid.

Then, in a process block 312 the substrate drying assembly support arm 130 is moved into position closely spaced above the substrate 114. The process block 312 is preferably at least partially performed concurrently with the process block 308.

As described above, the drying assembly 120 includes an outlet for applying liquid to the upper surface of the substrate and also includes an outlet for applying a drying vapor to the upper surface of the substrate. Next, in a process block 314, the substrate drying assembly support arm 130 is positioned so that the liquid applying outlet of the drying assembly 120 is located approximately over the center of the substrate 114. Any of the process blocks 308–320 could include increasing the rate of rotation of the substrate 114 to a second rate. The second rate of rotation of the substrate 114 is preferably much greater than the first rate of rotation of the substrate 114. At higher rates of rotation, processing liquid is flung off the substrate surfaces at a higher velocity. This increases the likelihood of splash-back. As mentioned above in connection with FIGS. 11B and 11C, the splash guard 134 is configured to minimize this. In the position shown in FIG. 11B, most of the periphery of the substrate 114 is below the upper edge of the splash guard 134. As shown in FIG. 11C, all of the periphery of the substrate 114 is below the splash guard 134. Thus, there is minimal area not protected from splash-back by the splash guard 134.

Then, in a process block 316, liquid is applied to the substrate 114 through the liquid applying outlet of the drying head 128. In one advantageous alternative, the process block 316 is implemented at least partially concurrently with the process block 314. In this way, the liquid is applied to the substrate 114 through the liquid applying outlet of the drying head 128 while the substrate drying assembly support arm 130 is moved to the center of the substrate 114. In a process block 318, the substrate drying assembly support arm 130 is retracted to a position where the drying outlet of the drying head 128 is positioned over the center of the substrate 114. In a process block 320, the tensioactive vapor is applied to the substrate 114 as the substrate 114 rotates. The vapor applied at the process block 320 dries the center of the substrate 114 due to the rotation and by the action of the vapor on the liquid on the surface of the substrate 114. In a process block 322 the substrate drying assembly support arm 130 is retracted radially outwardly at a controlled rate to the periphery of the substrate 114. As the substrate drying assembly support arm 130 is being withdrawn, liquid is applied to the substrate 114 through the liquid outlet of the drying head 128. The control of the retraction is discussed in more detail below. In the process block 322 the drying head 128 applies tensioactive vapor to the substrate 114 through the vapor applying outlet following the application of liquid. Then in a process block 324, when the drying head 128 approaches the periphery of the substrate, the application of liquid to the upper surface of the substrate 114 is stopped. In a process block 326, the retraction of the substrate drying assembly support arm 130 is stopped near the periphery of the substrate 114. In the process step 326 the rotational speed of the substrate 114 is also greatly increased. This tends to dry a lower surface of the substrate 114 by centrifugal action. Then, in a process block 328, the application of drying vapor to the substrate 114 is stopped before the drying head 128 is retracted beyond the outer periphery of the substrate 114. In an end block 330, the drying head 128 is retracted to the home position, the rotation of the substrate 114 is stopped, and the process is completed.

As mentioned above, one important consideration applied to the single wafer cleaning apparatus is through-put. Consequently, the process embodied in process steps 300–330 can be optimized to minimize cleaning, rinsing, and drying time. To this end, it will be appreciated that some of the above process blocks could be combined with the process still implementing the invention. For example, in one variation of the above process, process blocks 308, 310, and 312 are carried out at least partially concurrently. In another variation of the process described above, process blocks 318 and 320 could be carried out partially concurrently. Also, although the lower-numbered process blocks noted above generally begin before the higher-numbered blocks, many of the blocks are executed at least partially concurrently.

The process described above can be incorporated into a wide variety of cleaning and drying recipes. For example, one drying recipe for an 8 inch, or a 200 millimeter, substrate begins after the probe 122 is retracted in the process block 308. The process block 310 commences by rotating the substrate at the second rate, e.g. 300 RPM (the first rate of rotation being that required by the cleaning assembly 118). This second rate is maintained for 29 seconds. In the process block 310 the substrate 114 is rinsed for 5 seconds. The process block 310 also can include a hydrofluoric acid exposure.

The process block 312, which moves the substrate drying assembly support arm 130 toward a location over the center of the substrate 114, begins 4 seconds before the end of process block 310. In the process block 314, the substrate drying assembly support arm 130 is positioned so that the liquid applying outlet of the drying head 128 is located approximately over the center of the substrate 114. At the process block 316, liquid is applied to the substrate 114 through the liquid applying outlet of the drying head 128. This continues until process block 324. At the process block 318, the substrate drying assembly support arm 130 is retracted. When process block 318 is completed the drying outlet of the drying head 128 is positioned over the center of the substrate 114. At the process block 320, the tensioactive vapor is applied to the substrate 114. Next, at the process block 322, the substrate drying assembly support arm 130 is retracted radially outwardly while liquid and vapor are applied to the substrate 114 through the liquid and vapor outlets of the drying head 128 respectively. Next at the process block 324 the application of liquid to the substrate 114 is stopped. The retraction of the drying head 128 is stopped at the process block 326. Still at the process block 326 the rotational speed of the substrate 114 is greatly increased so as to dry a lower surface of the substrate 114. This increased speed is preferably 1000 revolutions per minute (RPM) or higher and is more preferably 1800 RPM. Finally, at the process block 328 the application of vapor to the substrate 114 is stopped and the drying head 128 is retracted beyond the outer periphery of the substrate 114. As mentioned, the above recipe is for an 8 inch, or a 200 millimeter, substrate. It will be recognized that the times may vary for different applications, including different substrate sizes.

Figure 21:
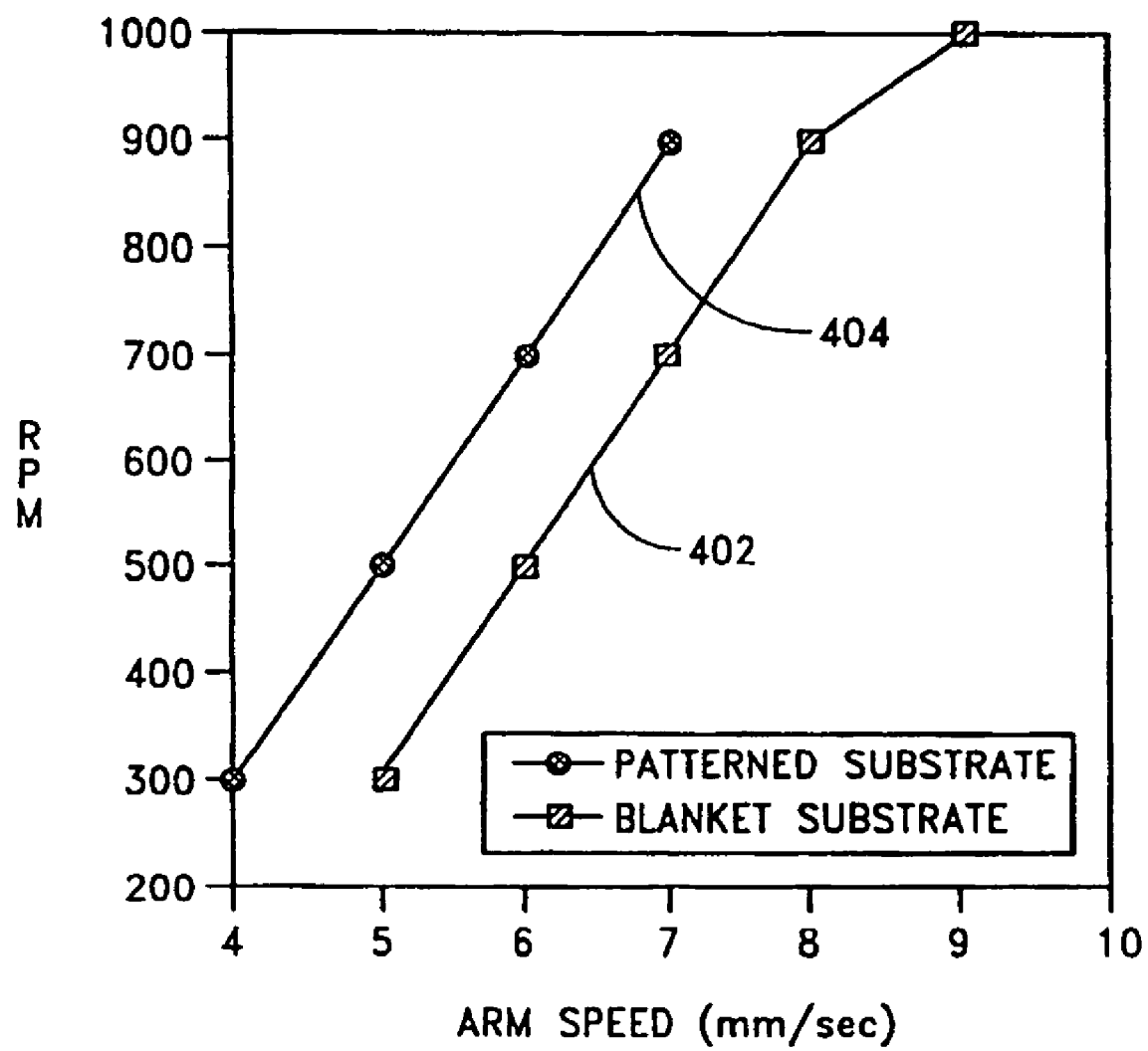
FIG. 21 shows a two-dimensional graph of patterned and blanket substrate process windows that relate the drying head retraction rate to the rotational speed of the substrate.

The cleaning apparatus disclosed herein also exploits a relationship between the rate of rotation of the substrate 114 and the rate at which the drive module 146 retracts the drying head 128. Generally, the faster the rotation, the faster the retraction can be. In some embodiments, it is desired to provide adequate drying in the shortest time. FIG. 21 provides one example relationship between substrate rotation rate and drying assembly retraction rate where it is desired to use a single, constant retraction rate. As may be seen in connection with FIGS. 22A–22B, higher retraction rates for the same rotation rate can be achieved under some conditions.

Referring now to FIG. 21, one example relationship between the rotation rate and the retraction rate is illustrated as a two-dimensional processing window. The x-axis of the processing window represents a range of rates at which the substrate drying assembly support arm 130 and the drying head 128 of the drying assembly 120 can be retracted. The y-axis represents the range of revolutions per minute (RPM) at which the chuck 110 can rotate the substrate 114. In the example relationship shown in FIG. 21, the substrate 114 can be rotated during the substrate top surface drying operation in a range between about 200 RPM and about 1,000 RPM while the substrate drying assembly support arm 130 can be retracted in a range between about 4 mm per second and about 9 mm per second. In another embodiment, the substrate 114 can be rotated during the substrate top surface drying operation in a range between about 50 rpm and about 1000 rpm, while the substrate drying assembly support arm 130 can be retracted in a range between about 1 mm per second and about 20 mm per second. It will also be understood that higher substrate rotational rates are possible and that, as shown in FIG. 21, such higher rotation rates will enable drying assembly retraction at rates higher than those shown in FIG. 21.

Two advantageous process windows governing the rate of retraction of the substrate drying assembly support arm 130 and the rate of rotation of the substrate 114 are further illustrated in FIG. 21. A line 402 represents a blanket substrate process window, which is a preferred relationship between the rate of retraction of the substrate drying assembly support arm 130 and the rate of rotation of a blanket substrate. A blanket substrate is one that has a uniform top surface. A line 404 represents a patterned substrate process window, which is a preferred relationship between rate of retraction of the drying assembly and the rate of rotation of a patterned substrate. A patterned substrate is one that has one or more features created on the top surface. The preferred rate of retraction of the substrate drying assembly support arm 130 for a blanket substrate is about 5 millimeters per second when the rate of rotation of the substrate 114 is about 300 RPM. The preferred rate of retraction of the substrate drying assembly support arm 130 for a patterned substrate is about 4 millimeters per second when the rate of rotation of the substrate 114 is about 300 RPM. As can be seen, the preferred rate of retraction can be increased by about 0.5 mm per second for each 100 increase in the RPM of substrate rotation. For blanket substrates that are rotated faster than 900 RPM, the preferred rate of retraction of the substrate drying assembly support arm 130 is increased as the rate at which the substrate 114 is rotated is increased about 1.0 mm per second for each 100 increase in the RPM of substrate rotation.

The blanket and patterned process windows shown in FIG. 21 also illustrate other alternative rates of retraction that perform a satisfactory dry for a given substrate rotational speed. For example, for blanket substrates the rate of retraction of the substrate drying assembly support arm 130 of the drying assembly 120 may be lower than the preferred rate while still performing a satisfactory dry. These lower rates are the retraction rates that are to the left of the line 402. Also, for patterned substrates, substrate drying assembly support arm 130 of the drying assembly 120 may be retracted at rates that are lower than the preferred rate while still performing a satisfactory dry. These lower retraction rates for patterned substrates are to the left of the line 404. Also, the rotation rate for a given retraction rate may be higher than (i.e. above on the graph) the preferred rate illustrated by the lines 402, 404.

Figure 22A:
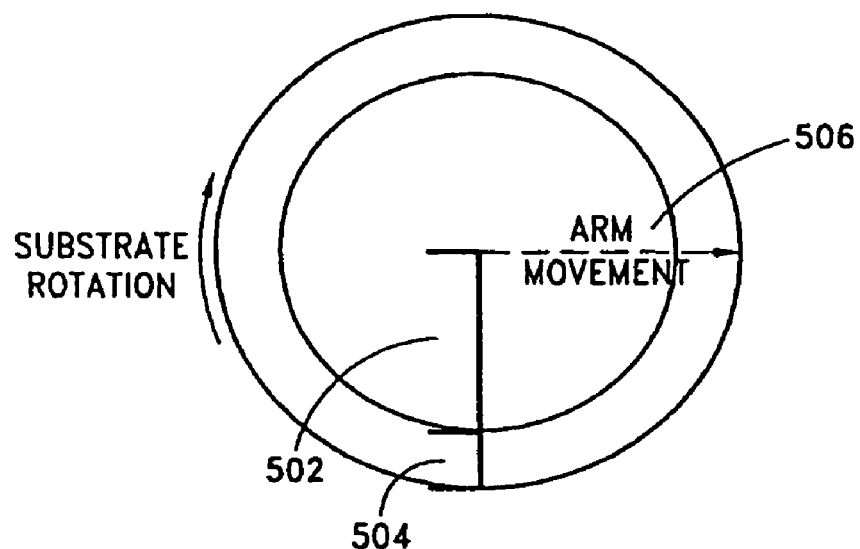
FIG. 22A shows a two-zone drying head retraction rate map.
Figure 22B:
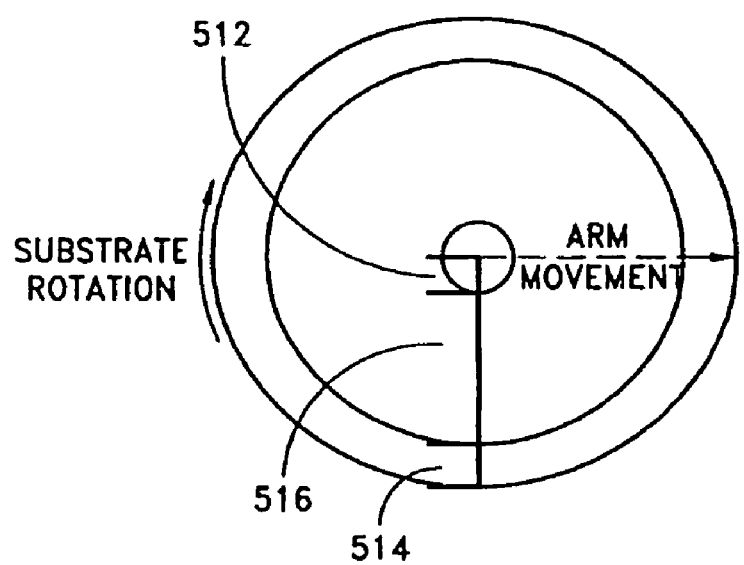
FIG. 22B shows a three-zone drying head retraction rate map.
Figure 23:
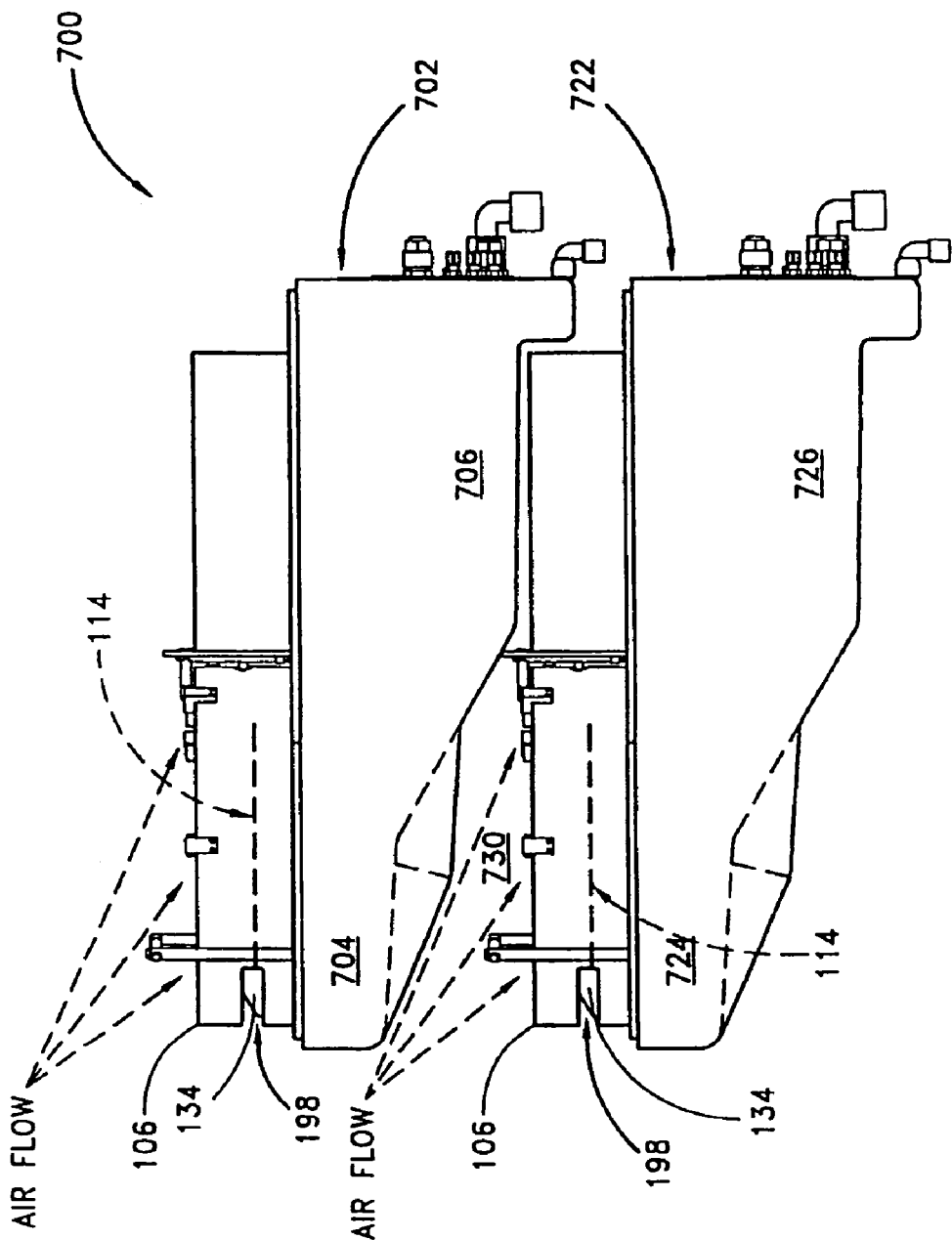
FIG. 23 shows a side elevation view of a stackable configuration of one embodiment of the substrate cleaning apparatus.

It has been found that some areas or zones in the substrate dry faster than others areas or zones. FIGS. 22A–22B illustrate that this relationship that can be exploited in order to manage cleaning efficiency and cleaning times (and, therefore, through-put). In other words, the process windows shown in FIG. 21 can be applied to the slowest drying zone. Other process windows reflecting faster drying assembly retraction rates can be implemented in the faster drying zones, as described below.

Referring now to FIGS. 22A–22B, the drying head 128 can be retracted at different rates as it is moved from the center of the substrate 114 to the edge of the substrate 114. In one embodiment illustrated in FIG. 22A, and preferred for blanket substrates, the substrate 114 is divided into a zone 502 near the center of the substrate 114 and a zone 504 near the periphery of the substrate 114. The dashed arrow illustrates the retraction of the substrate drying assembly support arm 130. The retraction rate near the center of the substrate 114 in the zone 502 is preferably faster than the retraction rate near the periphery of the substrate 114 in the zone 504 because the periphery of the substrate may dry more slowly.

Alternately for patterned substrates, as illustrated in FIG. 22B, the substrate 114 can be divided into a zone 512 near the center of the substrate, a zone 514 near the periphery of the substrate 114, and a zone 516 between the zones 512, 514. In one embodiment, the substrate drying assembly support arm 130 can be retracted while in the zone 516 at a rate faster than that in zone 512 near the center of the substrate 114 (the substrate-center retraction rate) and faster than that in zone 514 near the periphery of the substrate 114 (the substrate-periphery retraction rate). That is, the center of the substrate 114 may dry more slowly than the adjacent zone, but the center of the substrate 114 may dry faster than the periphery of the substrate 114.

It will be appreciated by one of ordinary skill in the art that the invention can also be embodied in control strategies that employ other numbers of zones and other locations on the substrate 114. It will also be appreciated that the retraction rate of the substrate drying assembly support arm 130 could be zero mm per second, i.e. the arm could be held still, for a period of time in one or more of the zones.

Referring now to FIGS. 6, 9A, 9B, and 23–25, the apparatus 100 described herein is uniquely arranged to be stackable and to be incorporated into a substrate processing system 700. The substrate processing system 700 comprises a first substrate cleaner 702 comprising a forward portion 704. The forward portion 704 includes a rotatable substrate support, or chuck 110, a dispenser 108 for applying fluid onto a substrate 114, and a probe 122 to be positioned closely spaced above the substrate to enable a meniscus of the liquid to be formed between the probe 122 and the substrate 114. The probe 122 is configured to loosen particles on the substrate in response to megasonic energy being applied to the probe 122.

The cleaner 702 also includes a rear portion 706 that is vertically thicker than the forward portion 704. The rear portion 706 includes a device for rotating the support 110, such as the servomotor 160, and one or more liquid or gas supply lines for conducting fluid to the dispenser 108. The rear portion 706 also includes a drive module 144 for moving the probe, as well as connections for applying megasonic energy to the probe.

The system 700 includes a second substrate cleaner 722. Like the substrate cleaner 702, the cleaner 722 includes a forward portion 724 and a rear portion 726 that is vertically thicker than the forward portion 724. In the system 700, the second cleaner 722 can be stacked below the first cleaner 702 with the forward portions being vertically aligned and the rear portions being vertically aligned. In this position, a space 730 is formed between the forward portions 704, 724 to permit ample gas flow into the space 730 between the forward portions of the cleaners. Stacking the first substrate cleaner 702 and the second substrate cleaner 722 reduces the cleanroom floor space which must be dedicated to cleaning and drying.

The vertical thickness of the bowl area is minimized by several related techniques. Utilizing the vertically fixed support chuck facilitates this by having the substrate handling robot provide the necessary vertical movement when transporting a substrate. A mechanism for vertically moving the chuck requires greater vertical space, which interferes with the air-flow to the substrate area. The slot 198 in the process bowl 106 enables use of the robot without increasing the space requirements because space beneath the substrate is desirable for applying liquid to the substrate lower surface. The moveable splash guard 134 permits the use of the slot 198 for substrate transfer.

Figure 24:
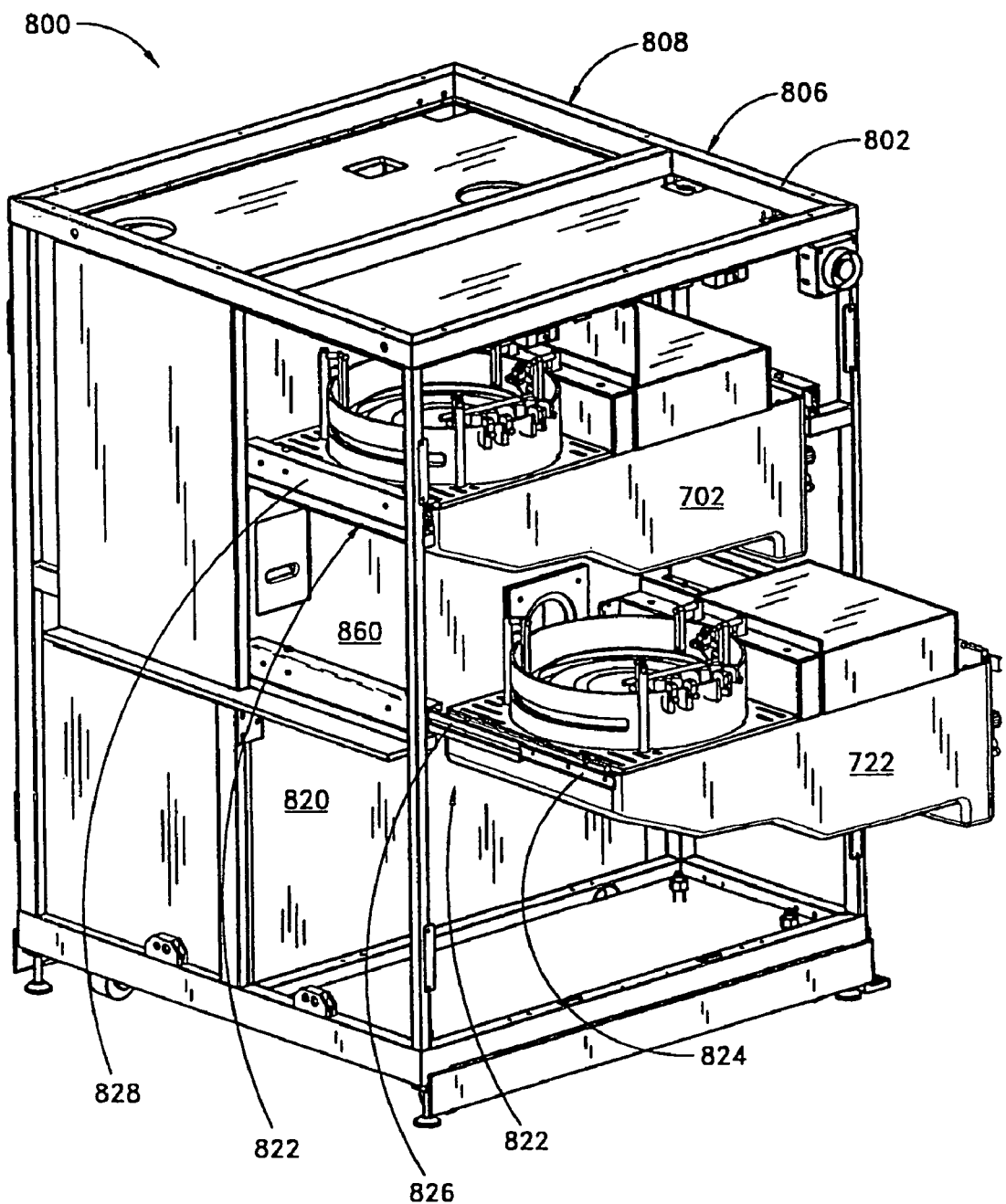
FIG. 24 shows a schematic perspective view of one embodiment of the stackable configuration substrate cleaning apparatus in a mounting system from the front side of the apparatus.
Figure 25:
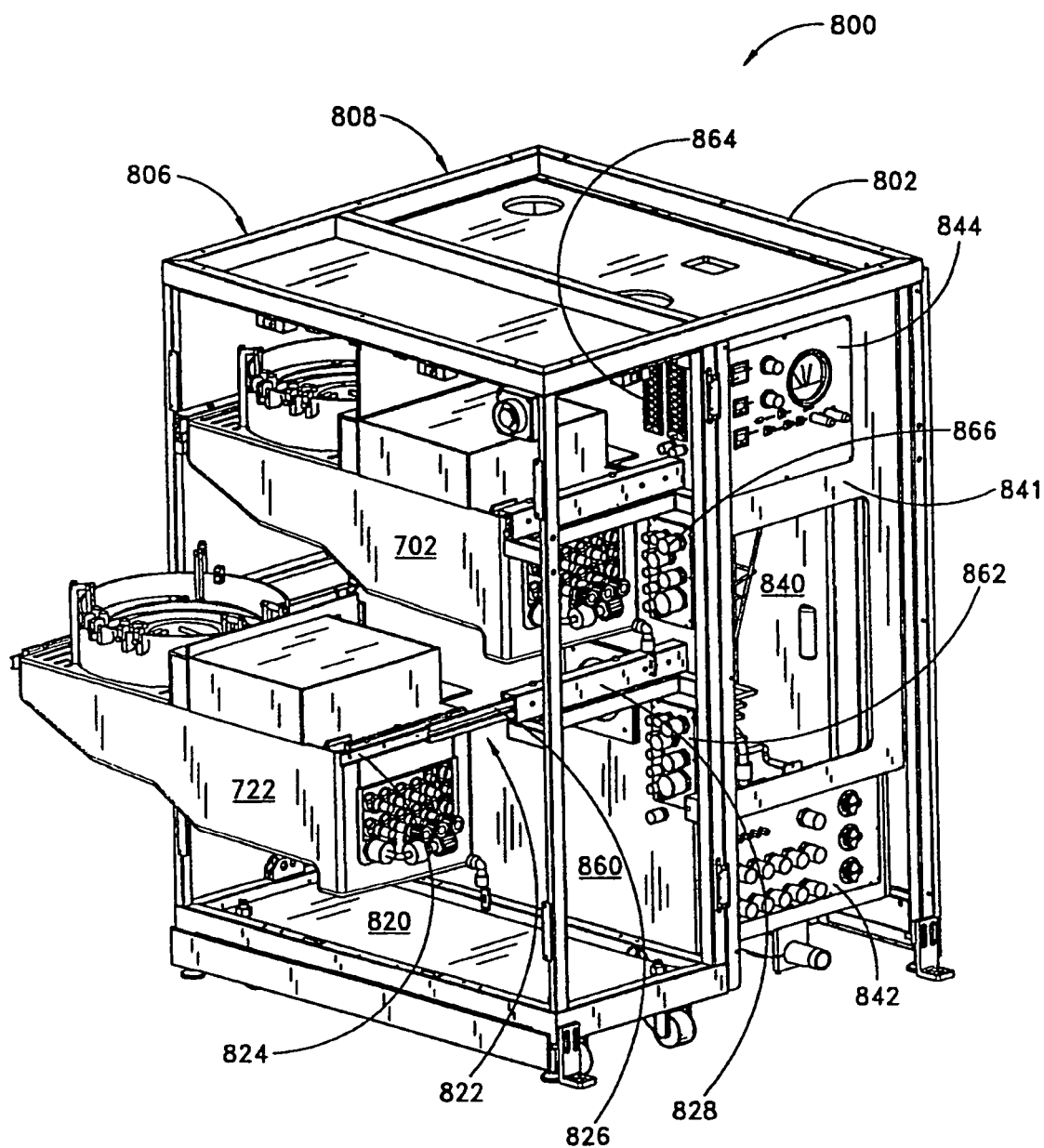
FIG. 25 shows a schematic perspective view of one embodiment of the stackable configuration substrate cleaning apparatus in the mounting system from the rear side of the apparatus.

As shown in FIGS. 24–25, the first and second substrate cleaners 702, 722 can be mounted into a stackable cleaner mounting system 800. The system 800 comprises a frame 802 defining a cleaner housing portion 806, and a plumbing and pneumatic support cabinet housing portion 808.

The cleaner housing portion 806 provides a space 820 where the cleaners 702, 722 are mounted. Each of the cleaners 702, 722 advantageously can be mounted on at least one drawer slide 822 comprising a cleaner fixture 824 mounted to the cleaner 722 or the cleaner 702, a translating portion 826, and a frame fixture 828 mounted to the frame 802. The fixtures 824, 828 can be configured to slideably interface with the translating portion 826. The fixtures 824, 828 preferably also are configured to support the weight of the cleaner 722 when it is within the housing portion 806 and when it is pulled out, as shown in FIGS. 24–25. Although shown retracted within the housing portion 806, the cleaner 702 also can be mounted to the frame 802 with a drawer slide 822. The cleaners 702, 722 are thus fixed vertically, but configured to translate horizontally so that they can be pulled out for inspection, testing, service, and maintenance. In one variation, the cleaners 702, 722 also could be mounted so as to be fixed vertically and horizontally, i.e. without the drawer slide 822.

The plumbing and pneumatic support cabinet housing portion 808 provides a space 840 in which a plumbing and pneumatic support cabinet 841 can be positioned. The cabinet 841 can include, for example, various liquid and gas hook-up lines, control lines, and the like. At least one external hook-up panel 842 can be provided to simplify the connection, maintenance, and exchange of the various fluid lines. Also, a control panel 844 can be provided to enhance the connection of a controller and one or more gauges for monitoring the performance of the cleaners 702, 722.

The pneumatic support cabinet 841 may include a shielding portion 860, one or more facility pass-through panels 862, and a pneumatic control signal panel 864. The shielding portion 860 shields the cleaners 702, 722 from the various components positioned within the cabinet 841 and also protects the components within the cabinet. The facility pass-through panels 862 provide one ore more convenient hook-up ports 866 for connecting the various fluid supply lines to the cleaners 702, 722. The pneumatic control signal panel 864 provides convenient pneumatic control hook-ups for the cleaners 702, 722.

It should be recognized that various modifications may be made to the embodiments illustrated without departing from the scope of the invention, and all such changes are intended to fall within the scope of the invention, as defined by the attended claims.

What is claimed is:

1. A method of drying a generally flat substrate that has been cleaned, the substrate positioned on a rotatable support, the method comprising the steps of:

selecting at least one of a blanket substrate drying process window if the substrate has a blanket portion and a patterned substrate drying process window if the substrate has a patterned portion;

moving a substrate drying assembly support arm into position closely spaced above the substrate, the substrate drying assembly including an outlet for applying liquid to an upper surface of the substrate and including an outlet for applying a drying vapor to the upper surface of the substrate;

rotating the substrate;

retracting the substrate drying assembly support arm radially outwardly according to the selected drying process window to a periphery of the substrate while applying liquid to the substrate through the liquid applying outlet and following that with said drying vapor being applied to the substrate to dry the substrate.

2. The method of claim 1, further comprising:

positioning the liquid applying outlet approximately over a center of the substrate;

applying liquid to the substrate through the liquid applying outlet;

positioning the drying vapor outlet approximately over the center of the substrate;

applying tensioactive vapor to the substrate as the substrate is rotating to thereby dry the center of the substrate due to the rotation and by the action of the vapor on the liquid;

wherein the positioning the liquid applying outlet, applying liquid, positioning the drying vapor outlet; and applying tensioactive vapor steps are performed before the retracting step.

3. The method of claim 1, wherein the blanket substrate drying process window comprises a range of retraction rates up to and including a maximum rate, and wherein the maximum rate is increased as the rate at which the substrate is rotated is increased by about 0.5 mm per second for about each 100 increase in the revolutions per minute of the rotation of the substrate, and wherein the maximum retraction rate is about 5 mm/sec when the rate of rotation of the substrate is about 300 revolutions per minute.

4. The method of claim 1, wherein the patterned substrate drying process window comprises the range of retraction rates up to and including a maximum rate, and wherein the maximum retraction rate is increased as the rate at which the substrate is rotated is increased by about 0.5 mm per second for about each 100 increase in the revolutions per minute of the rotation of the substrate, and wherein the maximum retraction rate is retracted is about 4 mm/sec when the rate of rotation of the substrate is about 300 revolutions per minute.

5. The method of claim 1, wherein during the drying operation of the upper surface of the substrate the substrate is rotated in a range between 50 rpm and 1,000 rpm while the retraction rate of the drying arm is in the range between about 1 and about 20 mm per second.

6. The method of claim 1, wherein during the drying operation of the upper surface of the substrate the substrate is rotated in a range between 200 rpm and 1,000 rpm while the retraction rate of the drying arm is in the range between about 4 and about 9 mm per second.

7. The method of claim 1, wherein the step of retracting the substrate drying assembly support arm comprises using a stepper motor to retract the substrate drying assembly support arm.

8. The method of claim 1, wherein the retraction rate comprises a range of rates up to and including a maximum rate, and wherein the maximum rate is increased as the rate at which the substrate is rotated is increased at a rate of at a rate of about 0.5 mm per second for each 100 increase in the revolutions per minute of the rotation of the substrate.

9. The method of claim 8, wherein the maximum rate at which the drying arm is retracted is 5 mm/sec when the rate of rotation of the substrate is 300 revolutions per minute.

* * * * *